Figure 1:
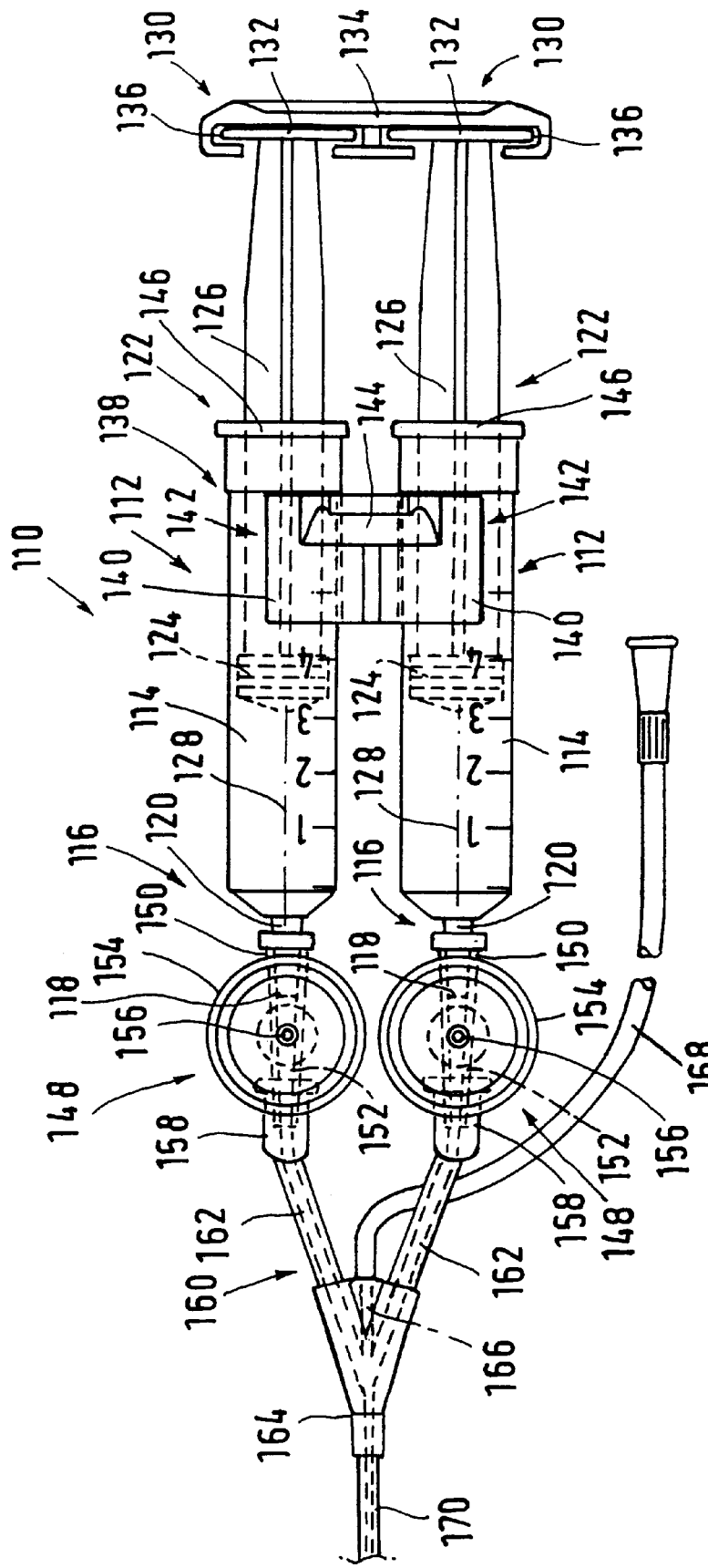

United States Patent [19]
Zinger et al.

[11] Patent Number: 6,113,571
[45] Date of Patent: Sep. 5, 2000

[54] APPLICATOR DEVICE FOR APPLYING A MULTIPLE COMPONENT FLUID

[75] Inventors: Freddy Zinger, Raanana; Igor Denenburg, Rehovot, both of Israel

[73] Assignee: Omrix Biopharmaceuticals S.A., Brussels, Belgium

[21] Appl. No.: 09/254,552

[22] PCT Filed: Sep. 10, 1996

[86] PCT No.: PCT/EP96/03975

§ 371 Date: May 10, 1999

§ 102(e) Date: May 10, 1999

[87] PCT Pub. No.: WO98/10703

PCT Pub. Date: Mar. 19, 1998

[51] Int. Cl.[7] .................................................. A61M 37/00
[52] U.S. Cl. ............................................ 604/82; 604/191
[58] Field of Search .................................. 604/82, 83, 85, 604/89, 91, 191, 218; 222/137

[56] References Cited

U.S. PATENT DOCUMENTS

| | | |
|---|---|---|
| 2,322,753 | 6/1943 | Thomas . |
| 5,104,387 | 4/1992 | Porkorney et al. . |
| 5,176,658 | 1/1993 | Ranford . |
| 5,445,614 | 8/1995 | Haber et al. ..................... 604/191 X |
| 5,474,540 | 12/1995 | Miller et al. ..................... 604/191 |
| 5,665,067 | 9/1997 | Linder et al. ..................... 604/82 |

FOREIGN PATENT DOCUMENTS

| | | |
|---|---|---|
| 0292472 | 11/1988 | European Pat. Off. . |
| 632579 | 12/1933 | Germany . |
| 295 16 650 U | 12/1995 | Germany . |
| 9001959 | 3/1990 | WIPO . |

*Primary Examiner*—John D. Yasko

[57] ABSTRACT

The applicator device comprises a plurality of supply containers (112), each of which is mechanically connected via fluid control device (148) to a common connecting headpiece (160). Each fluid control device (148) is provided with a first port (152) connected to said common connecting headpiece (160). A second port (150) of each fluid control device (148) is connected to a syringe body (114). Further, each fluid control device (148) comprises a third port adapted to have a medicinal vessel connected therethrough. Said third port is provided with an adaptor (154) for receiving said medicinal vessel and is further provided with a fluid conduit member which, when the vessel is received in the adaptor (154), extends into the interior of the vessel. Each flow control member is selectively movable from a first flow control position enabling a flow path between a first pair of two ports of the fluid control device and a second flow control position enabling a flow path between a second pair of two ports of the fluid control device, each flow control member being coupled to one of that ports for manipulation between said flow control positions.

12 Claims, 22 Drawing Sheets

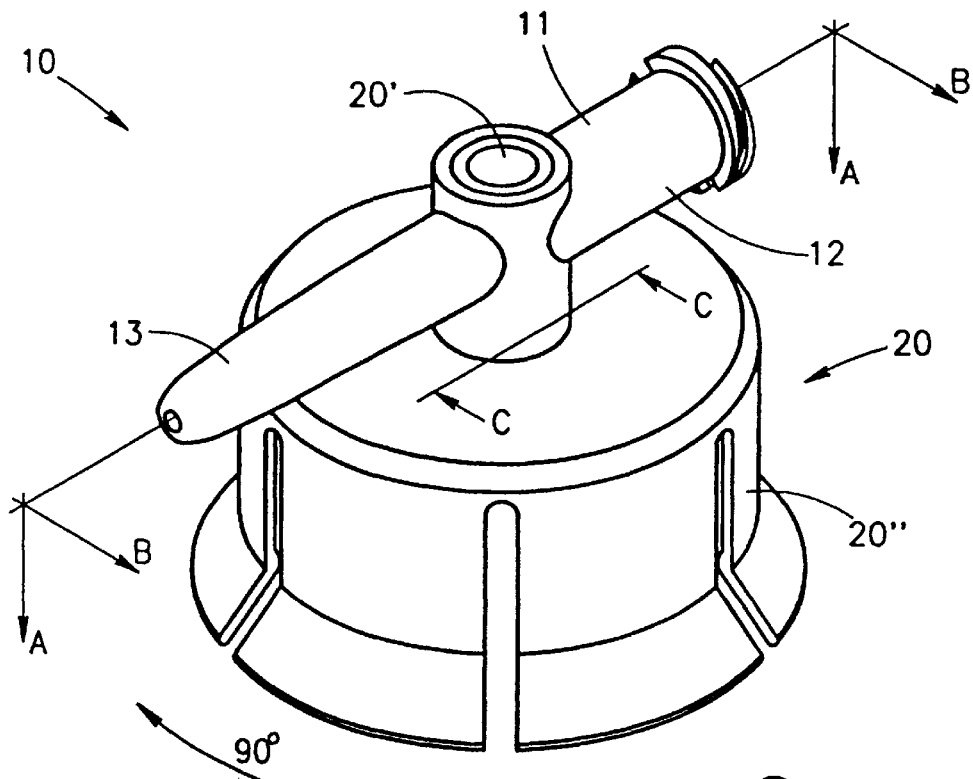
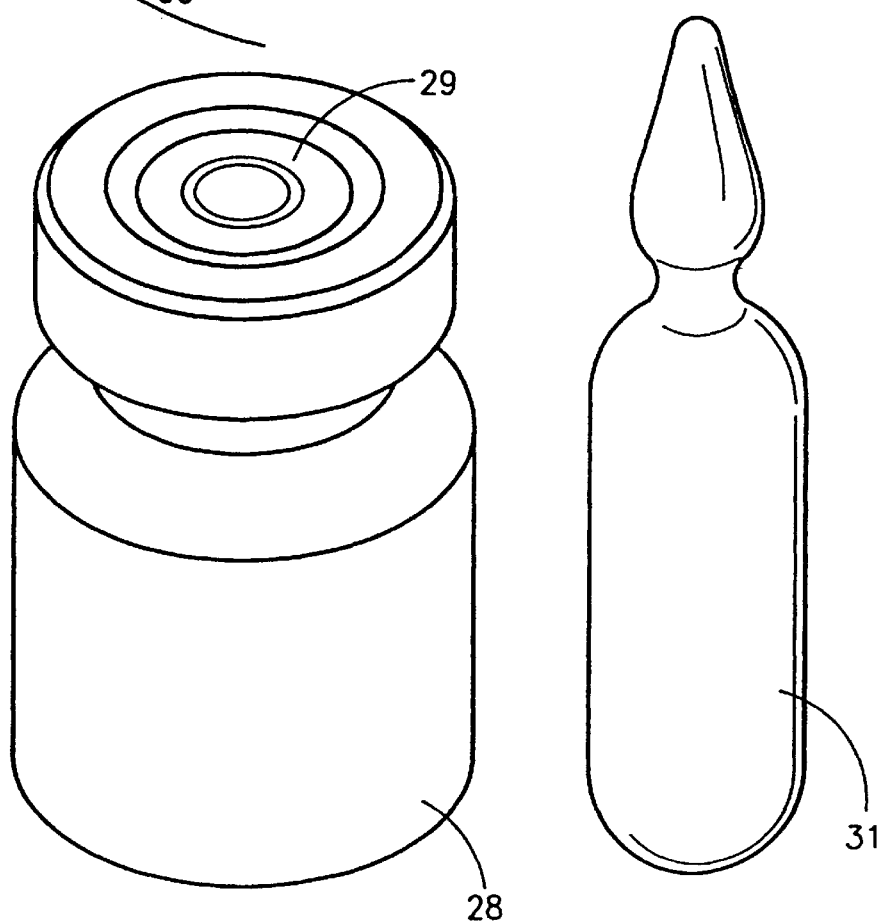
FIG.2

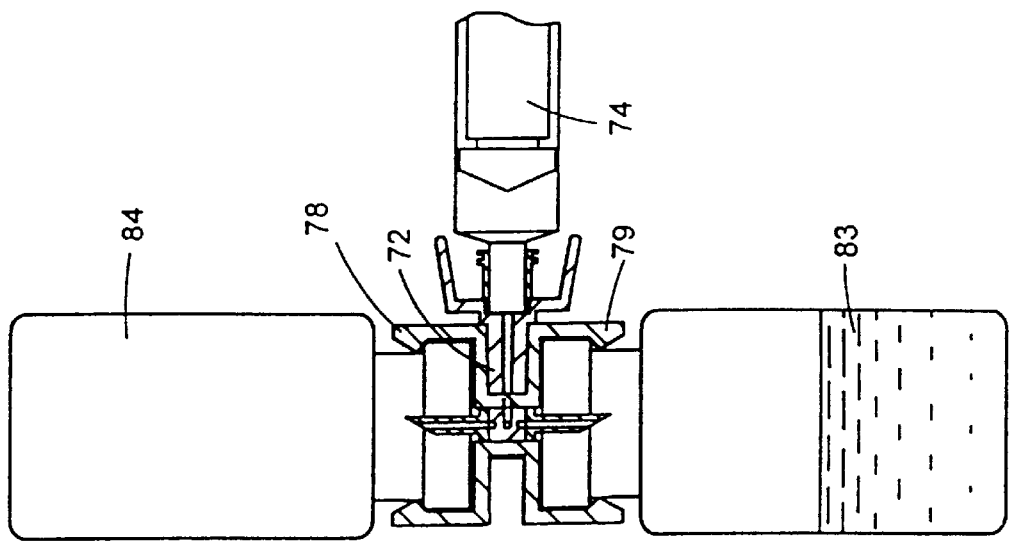
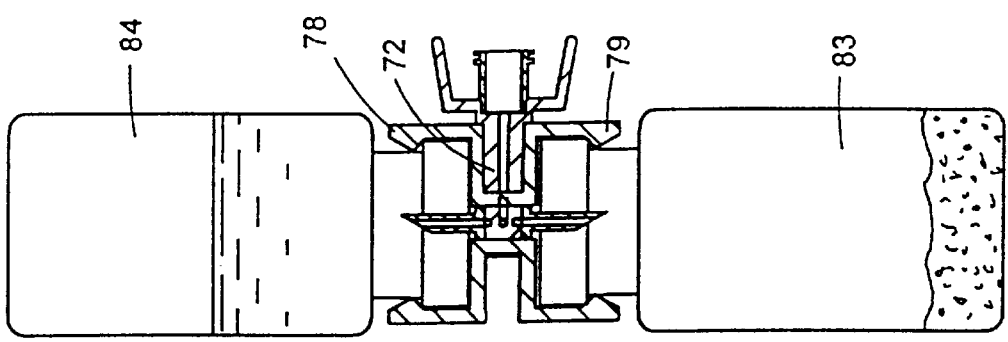
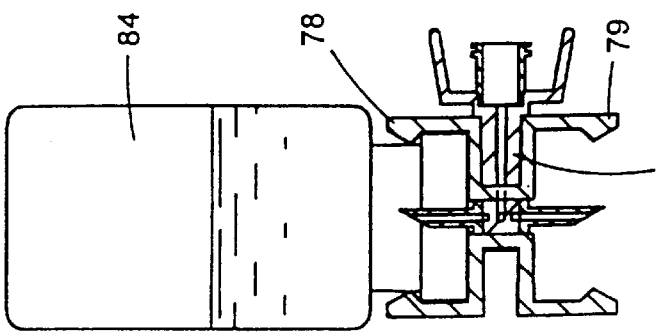
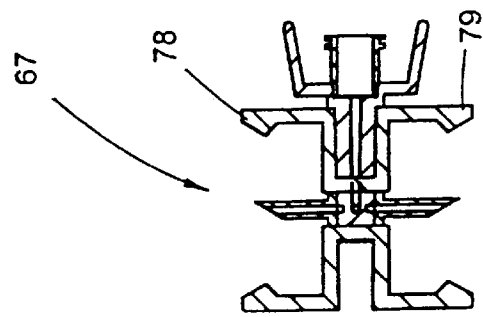

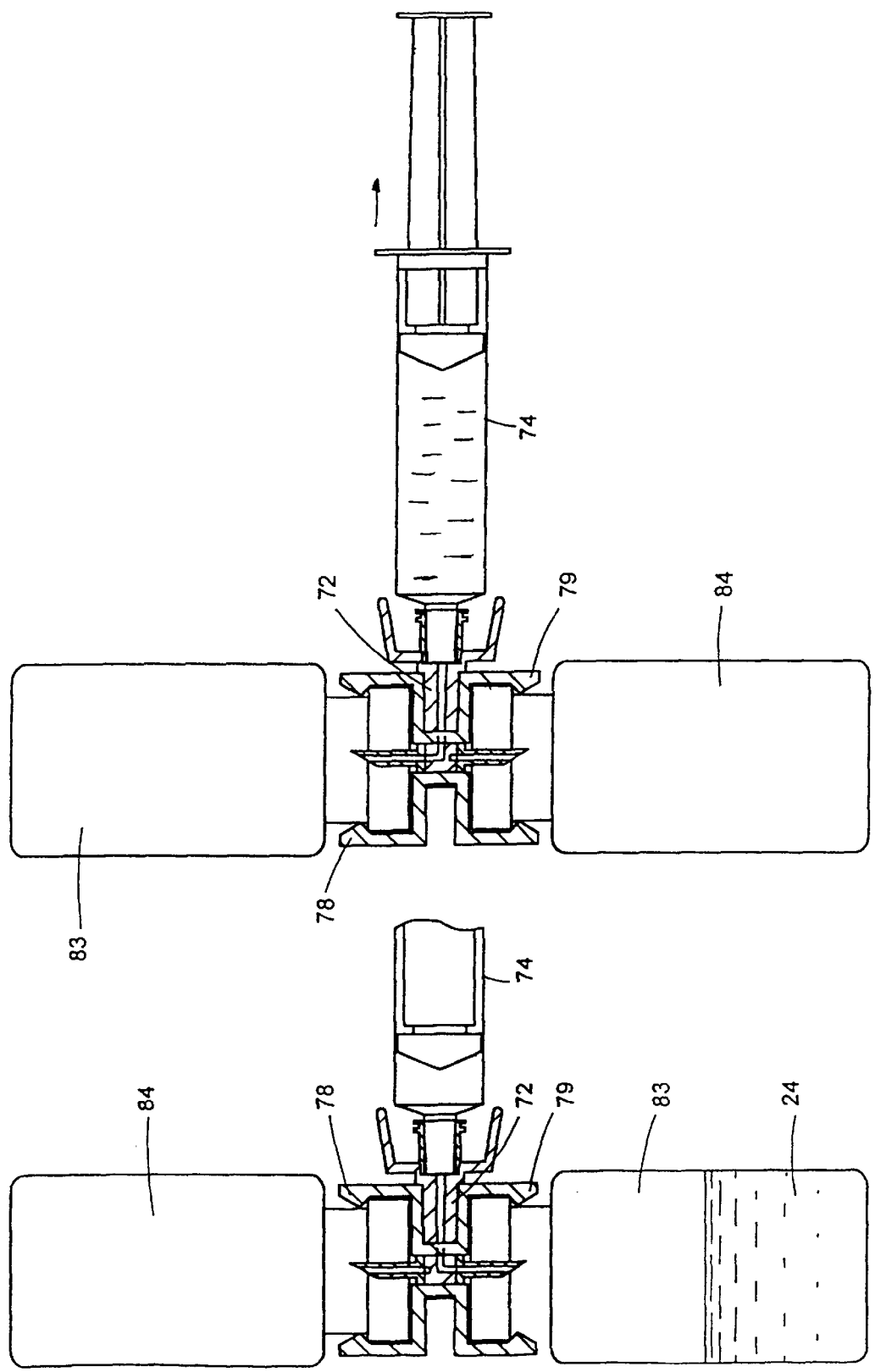

APPLICATOR DEVICE FOR APPLYING A MULTIPLE COMPONENT FLUID

This application is the national phase under 35 U.S.C. §371 of prior PCT International Application No. PCT/EP96/03975 which has an International filing date of Sep. 10, 1996 which designated the United States of America.

The present invention relates to an applicator device for applying a multi component fluid, especially a multi component tissue glue. Particularly, the invention relates to the straightforward and sterile loading of such an applicator device with the individual fluid components.

Applicator devices for medical multi component fluids are known e.g. from U.S. Pat. Nos. 4,874,368, 4,978,336, EP 0 037 393 B1 and WO 95/31137. All of these applicator devices comprise a plurality of substantially cylindrical supply containers for respectively one component of the fluid to be applied. These supply containers are normally provided as syringe bodies. Said syringe bodies include a cylindrical receiving chamber for the fluid component, having a piston with piston rod displaceably guided therein. The outlet ends of the syringe bodies are formed as conically tapered connecting pieces. The conically tapered ends of the syringe bodies are inserted into the connecting recesses of a connecting headpiece, the connecting headpiece being formed with individual channels extending therethrough from the connecting recesses to an outlet end of the connecting headpiece. When, in the filled condition of the syringe bodies, the piston rods are actuated, the fluid components will be discharged via the discharge ends of the syringe bodies and through the channels of the connecting headpiece to issue from the outlet ends of the connecting headpiece, thus allowing the fluid components to be applied for the gluing of tissue. To facilitate the handling of the applicator device, the applicator device is usually provided with a mounting support for the individual supply containers which is suited to be engaged thereunder by two fingers of a hand. The piston rods of the supply containers are connected to each other by a attachable connecting element so that, when pressure is exerted on the connecting element, a plurality of piston rods are actuated simultaneously.

The above outlined known tissue glue applicator devices are prepared for use in the following manner. First, the individual syringe bodies are filled with the fluid components. After all of the syringe bodies (normally, there will be two syringe bodies) have been filled with the different components, the syringe bodies are attached to the connecting headpiece and connected to each other by means of the mounting support. Finally, the connecting element is mounted on the operating ends of the piston rods. In view of the necessity to perform all of these processes under sterile conditions, the handling is rather bothersome and thus involves the risk of contamination.

It is an object of the invention to provide an applicator device for applying a multi component fluid, especially a multi component tissue glue, wherein the loading of the applicator device with the individual fluid components and the preparation of the device for applying a multi component fluid are simplified.

For solving the above object, the invention provides an applicator device for applying a multi component fluid, especially a multi component tissue glue, comprising a plurality of substantially cylindrical supply containers for respectively one component of the fluid to be applied, each of said supply containers having a front end with an opening for dispensing the fluid component from the supply container, a rear end facing away from the front end, and a slideably displaceable piston having a piston rod extending out of said rear end for operating the piston, and a connecting headpiece provided with connectors for fluid connection with the front ends of the supply containers, said connecting headpiece having channels for the individual components of the fluid to be applied extending therethrough from said connectors to an outlet end.

Further, in an applicator device of the above type, at least one fluid connection is provided with a fluid control device arranged between the supply containers and the connecting headpiece, said fluid control device comprising two ports connected to the supply container and the connecting headpiece. The fluid control device is additionally provided with a further connecting port. This third connecting port is provided with an adaptor serving for receiving a medicinal vessel and comprising a fluid conduit member. When the medicinal vessel is attached to said adaptor, said fluid conduit member extends into the interior of the medicinal vessel. The fluid control device is further connected to a flow control member which is selectively movable into one of two fluid control positions. In the first fluid control position, a flow path exists between a first pair comprising two of said three ports of the fluid control device, whereas, in the second fluid control position, a flow path exists between a second pair comprising a different combination of two of said three ports of the fluid control device. The flow control member is coupled to one of the ports so as to be operable from outside to be moved between the two flow control positions.

According to the invention, the loading of the applicator device and the preparation of the device for applying a multi component fluid are extremely simple. For loading the supply containers, the applicator device can remain in its assembled state required for applying the fluid. An intermediate removal of the supply containers from the connecting headpiece is not necessary. Instead, each fluid control device is preset to the first flow control position; in this first flow control position, a flow path exists between the second port, connected to the supply container, and the third port. When, in this first flow control position of the flow control member, a medicinal vessel is connected to the adaptor of the third port, the contents of the medicinal vessel can be sucked from said vessel into the supply container connected to this fluid control device. In this manner, all of the supply containers (normally, there will be two supply containers because use is made mostly of two component tissue glues) are loaded with a fluid component. After the individual supply containers have been loaded, the flow control members of the fluid control devices connected to the supply containers are moved into the second flow control position in which the second ports connected to the supply containers are in fluid connection with the first ports of the fluid control devices which are connected to the connecting headpiece connectors. Thus, the applicator device is ready for use because, upon actuation of the piston rods, the contents of the supply containers will be directly moved through the fluid control devices and the connecting headpiece to the outlet end of the connecting headpiece. At this outlet end, the two components will mix with each other and jointly provide for the desired effect of the tissue glue.

Thus, the decisive advantage yielded by the inventive applicator device resides in the extremely simple handling of the applicator device during the process of loading the individual supply containers. The handling steps required for this purpose are reduced to a minimum so that under this aspect the danger of contamination is considerably reduced (a so-called aseptically closed system). It is particularly advantageous that, when the supply containers are loaded, the applicator device is already in the assembled condition required for the later application process. Thus, at this point of time, the supply containers are already connected (via the fluid control devices) to the connecting headpiece. Further, at this point, also the elements required for handling the applicator device while applying the tissue glue are already in their mounted condition. These elements include e.g. a mounting support receiving the supply containers, and a connecting element for connecting the operating ends of the piston rods. Also other or respectively different elements or components required for handling the applicator device can be mounted already beforehand.

In accordance with the teachings of the present invention, there is provided a family of fluid control devices to be used in tissue glue applicator devices which are adapted for the aseptic application of tissue glue either directly of indirectly to an application site. The selection of the most suitable fluid control device in particular depends on the type of fluid to be applied and/or the manner in which it is packaged. Some of the devices are designed to enable the reconstitution of a fluid component provided in a powder form or as a liquid concentrate. Some of the devices are suited for vials or ampoules containing a single dose of a fluid whilst others are suited for vials or IV bags containing multiple doses.

In a preferred embodiment of a fluid control device, the flow control member is rotatably mounted in a body member so as to be selectively rotatable between its first flow control position and its second flow control position.

The adaptor can be integrally formed with the flow control member and designed so as to readily broken off therefrom after rotation of the flow control member from its first flow control position to its second flow control position. Alternatively, the adaptor can be detachably engaged to the flow control member by means of an interengaging means enabling axial detachment of the adaptor from the body member on a relative rotation therebetween to a position which urges the flow control member from its first flow control position to its second flow control position.

In a preferred embodiment of a fluid control device suitable for use with fluid components which require reconstitution, the fluid control device includes a fourth port in the form of an adaptor for enabling the attachment of a second medicinal vessel to the body member.

In a preferred embodiment of a fluid control device, the first port is also provided with an adaptor adapted for attachment thereto of a medicinal vessel and, in this case, the port adapted for receiving the syringe is rotatably coupled to the flow control member.

In each case, the adaptor can be adapted for attachment thereto of a vial, an ampoule or an IV bag, the former requiring that the fluid conduit member be formed as a puncturing tool for piercing the vial's rubber stopper on its attachment thereto. In the case of attachment of an ampoule, because the ampoule cannot be inverted, the fluid conduit member is required to be provided as a long straw to enable all or nearly all of its contents to be aspirated therefrom.

The adaptor can also include a conduit for venting the vessel when attached thereto. The conduit can include a filter for filtering the air traversing therethrough. The filter can be deployed within a lateral cavity provided within the adaptor or, alternatively, the filter can be provided as a discrete element exterior to the fluid control device.

Figure 3:
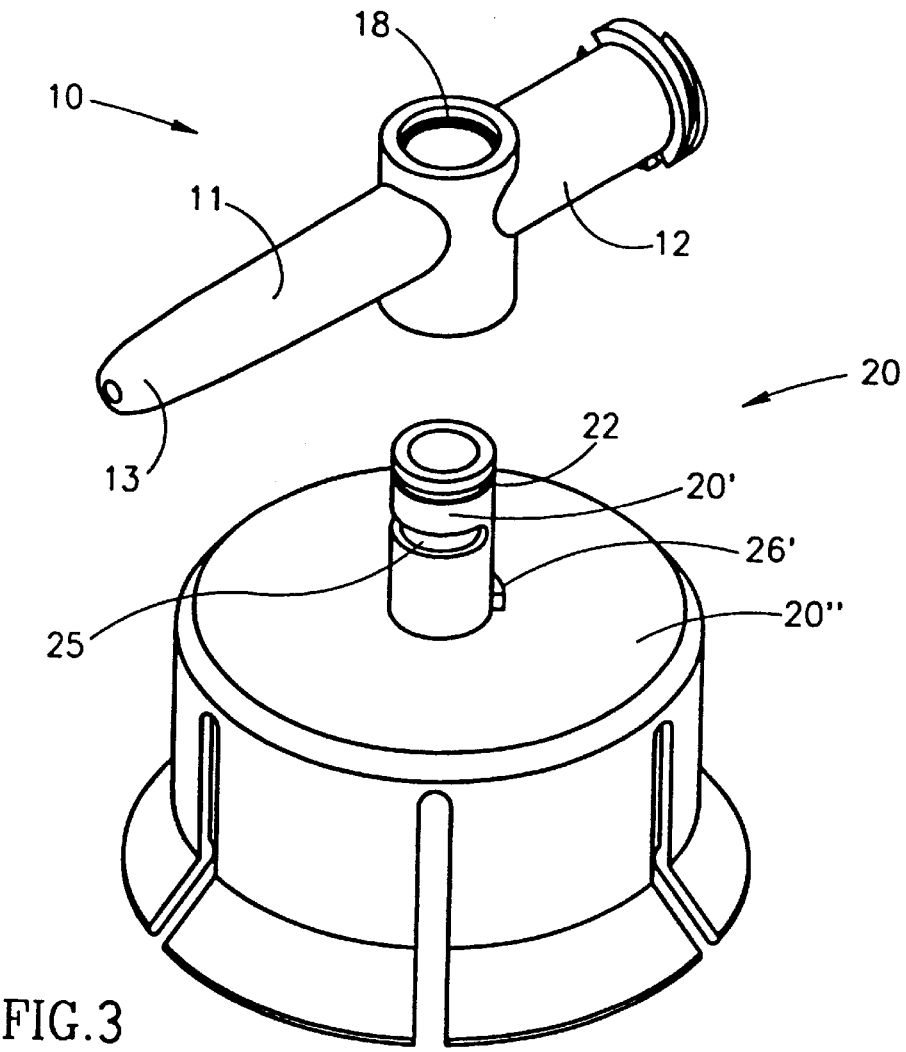
Figure 6:
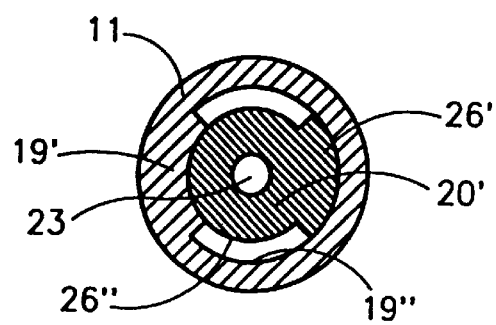
Figure 4:
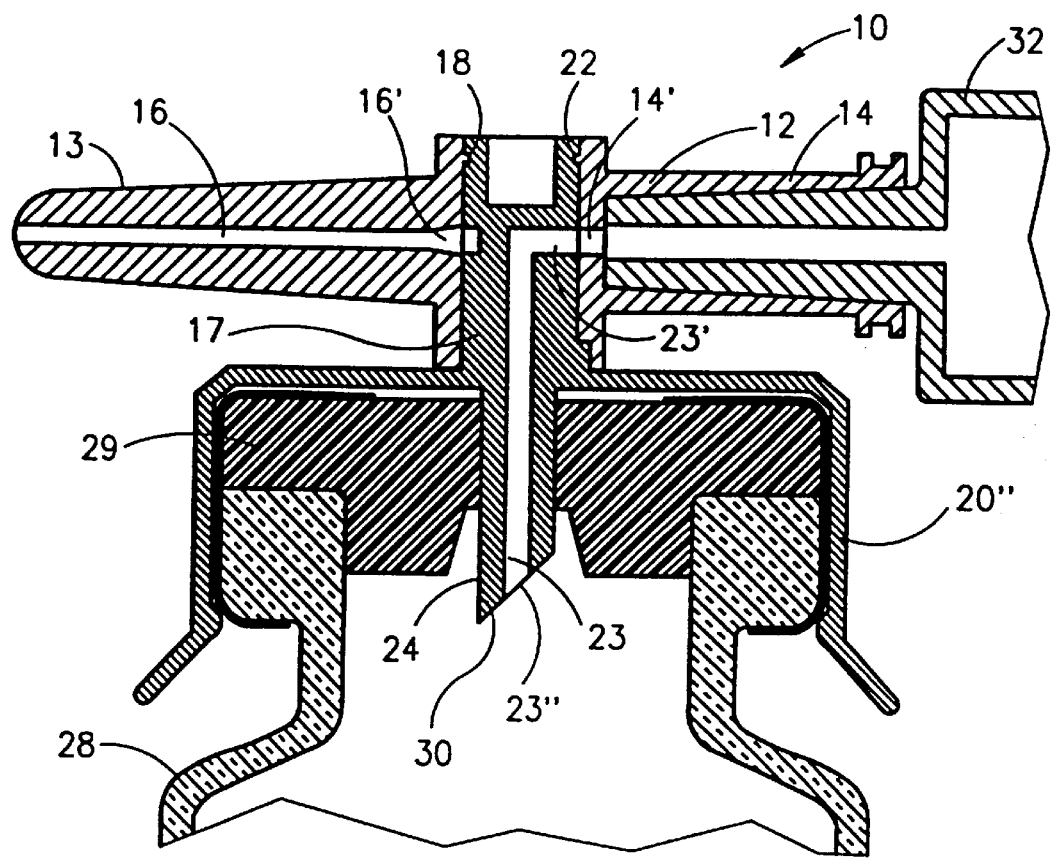
Figure 5:
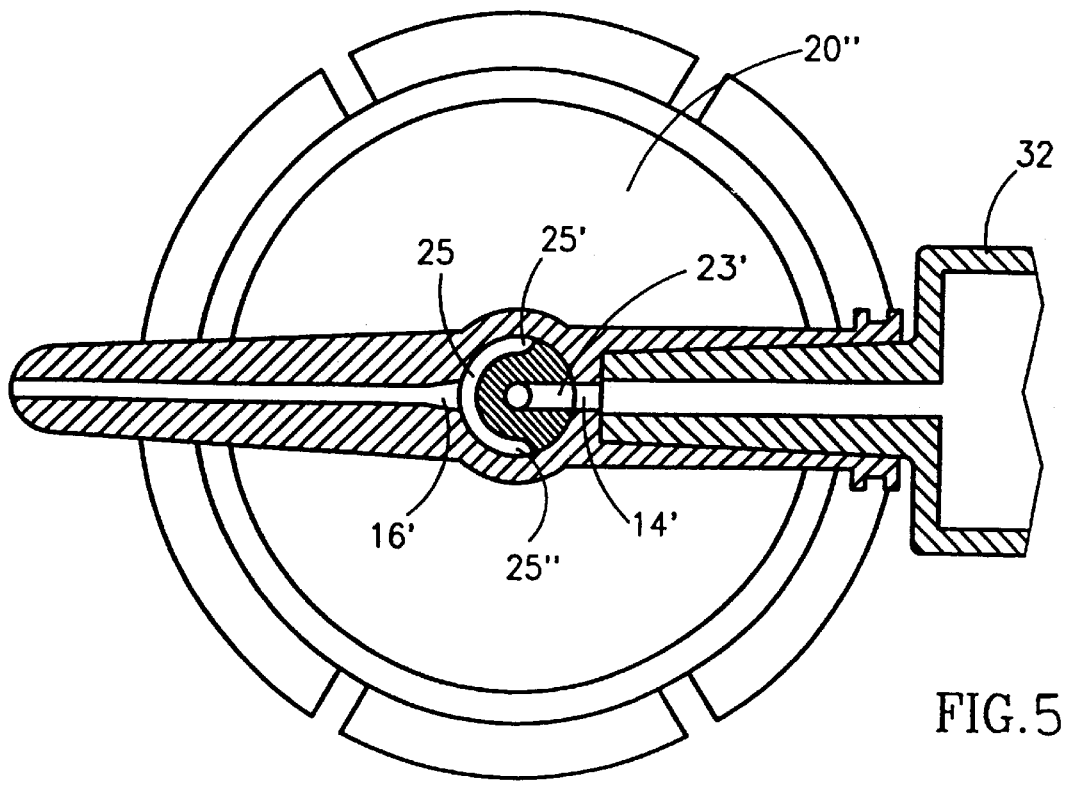
Figure 7:
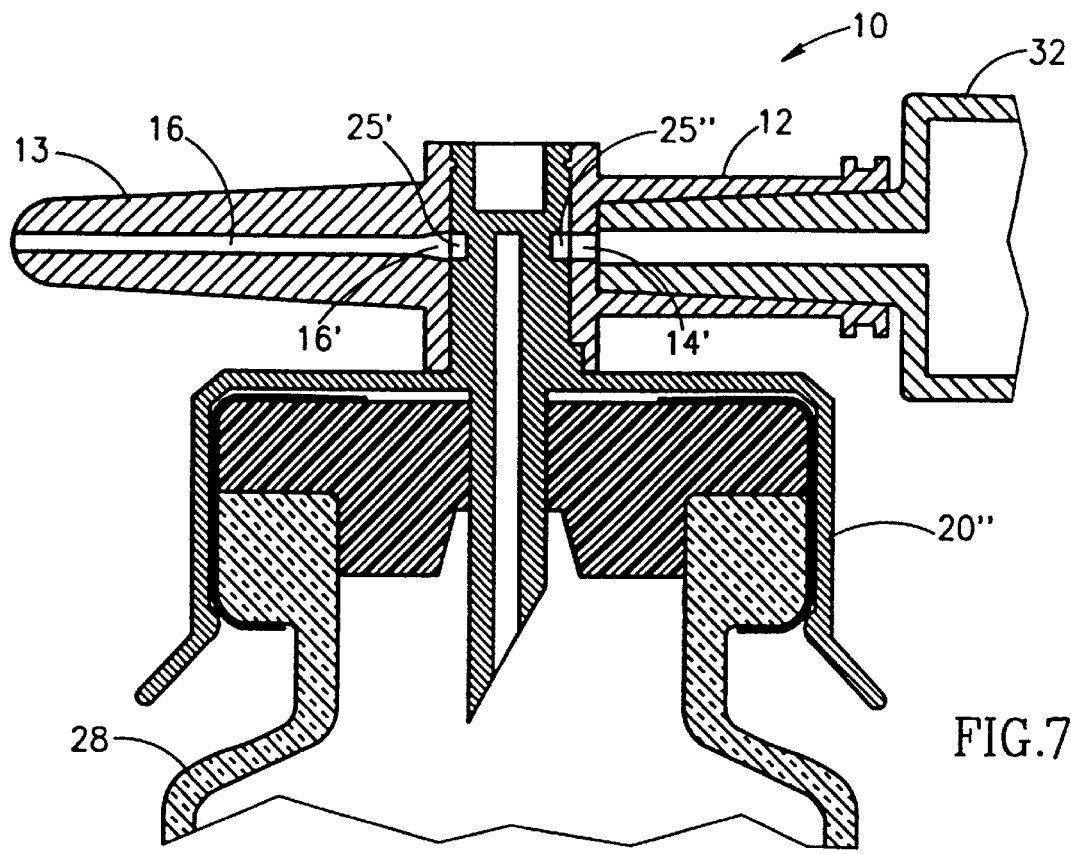
Figure 8:
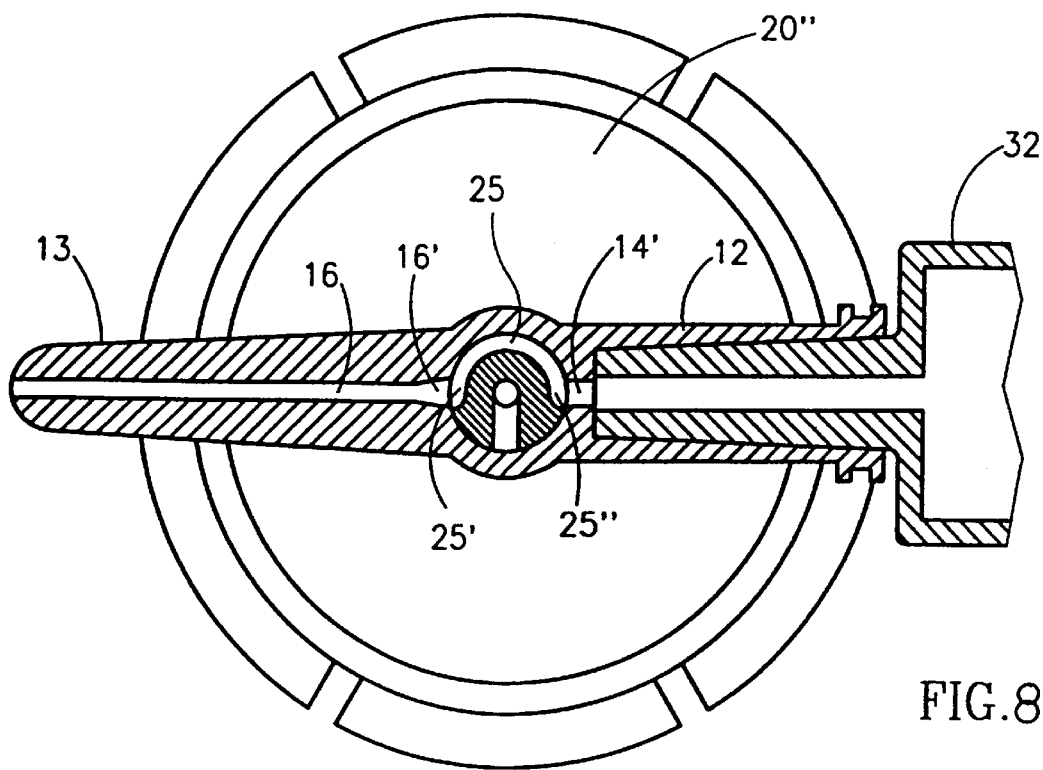
Figure 9:
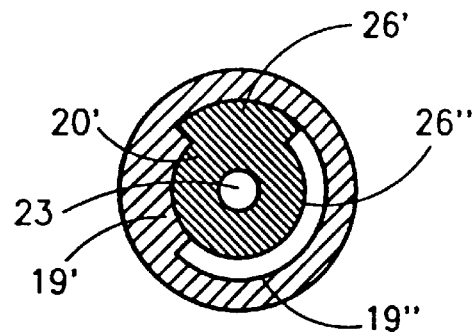
Figure 10:
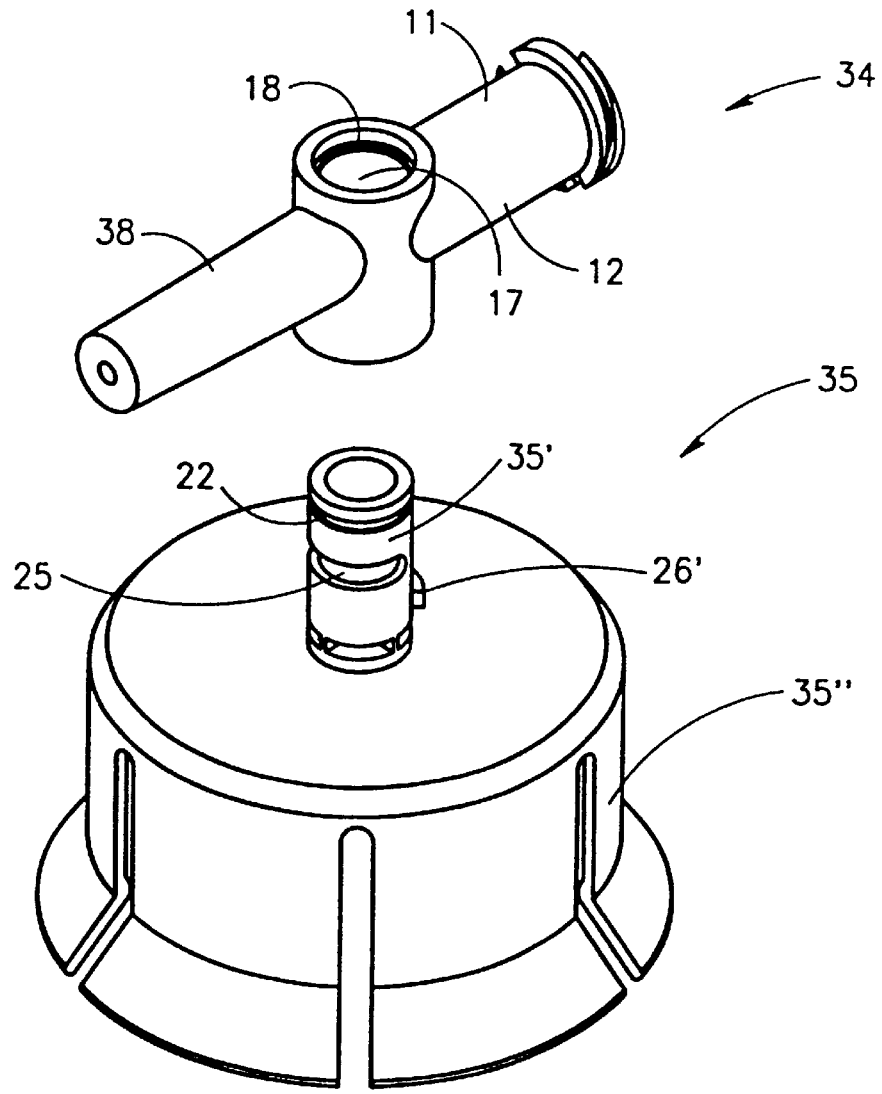
Figure 11:
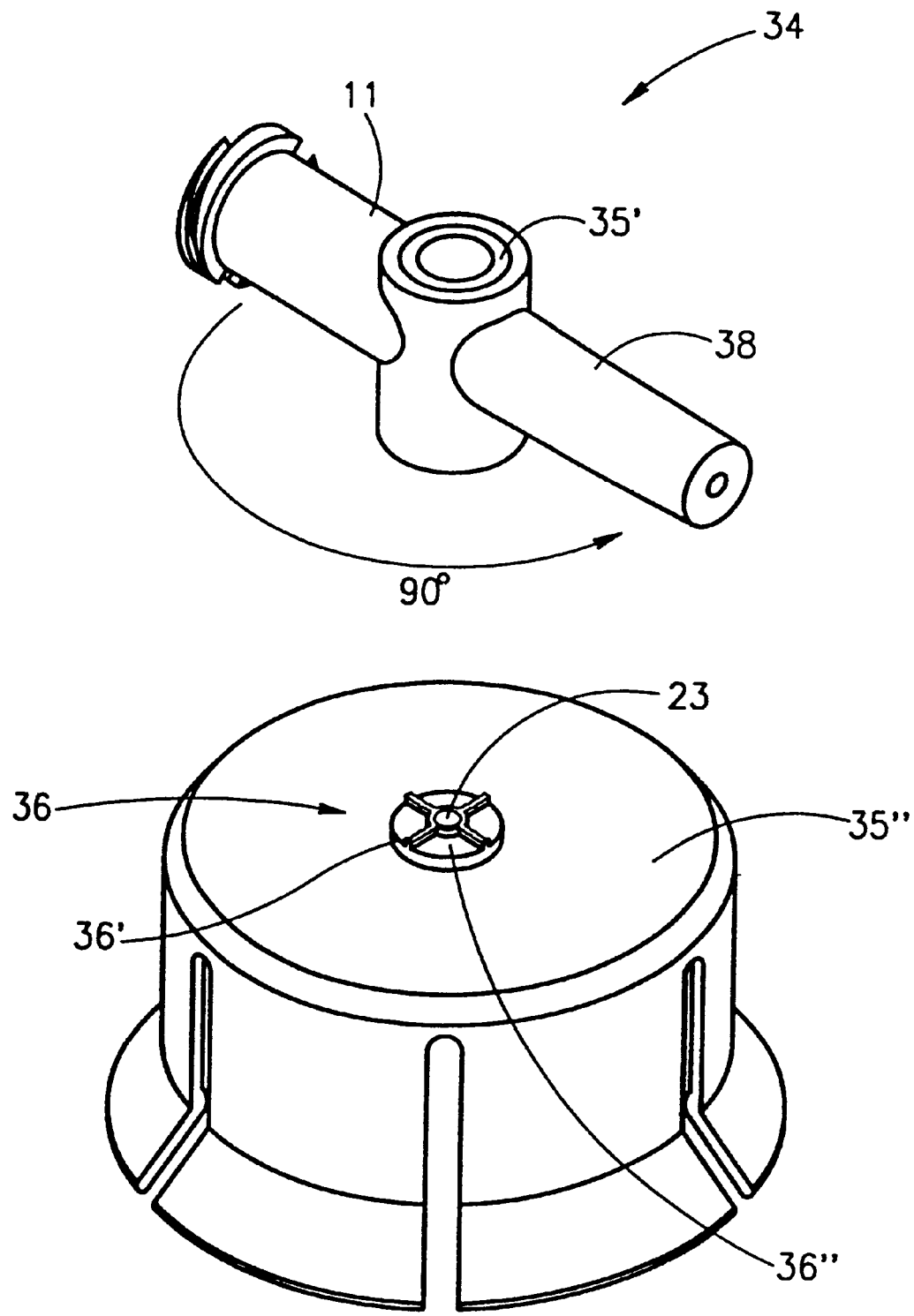
Figure 12:
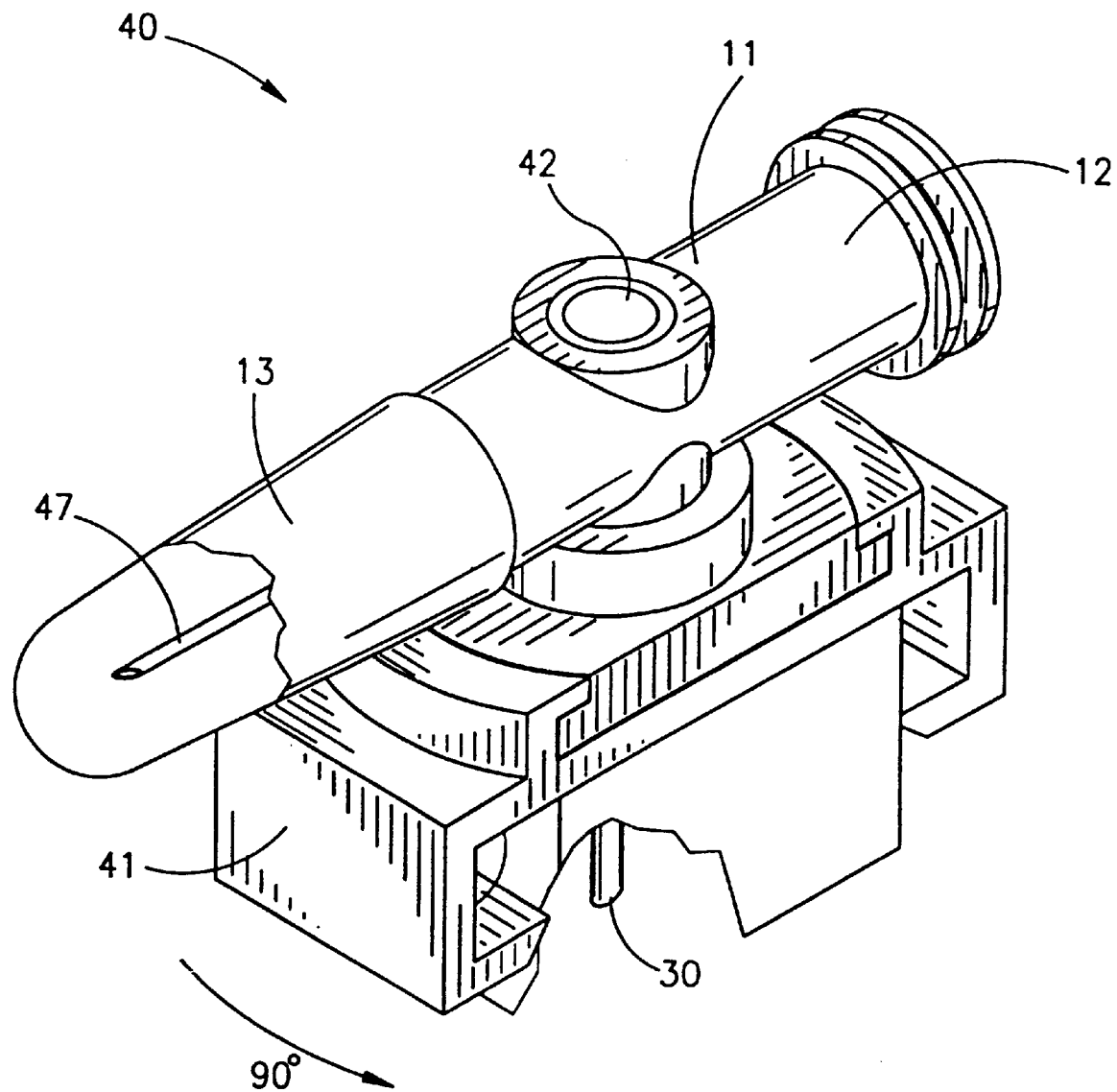
Figure 13:
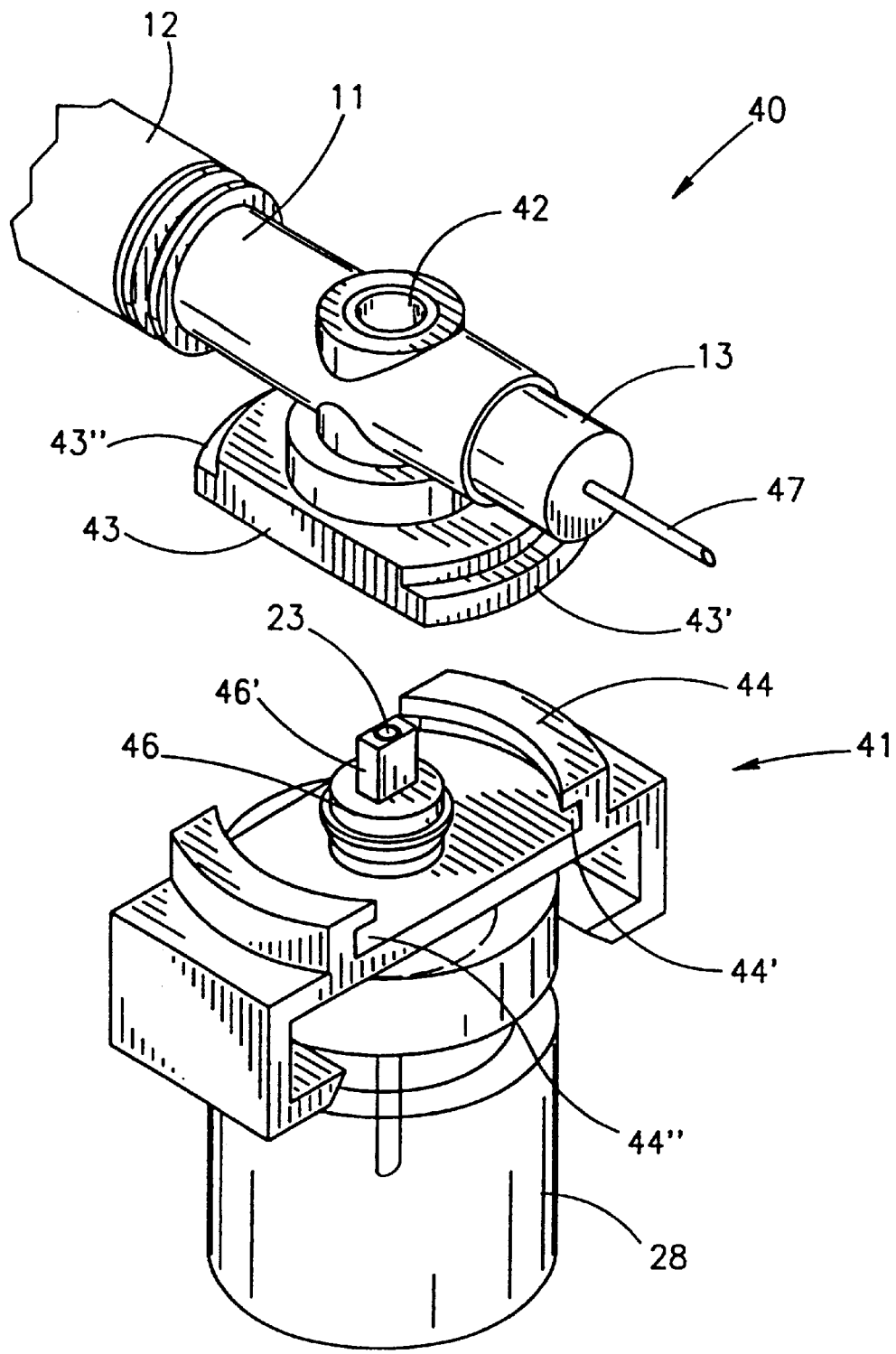
Figure 14:
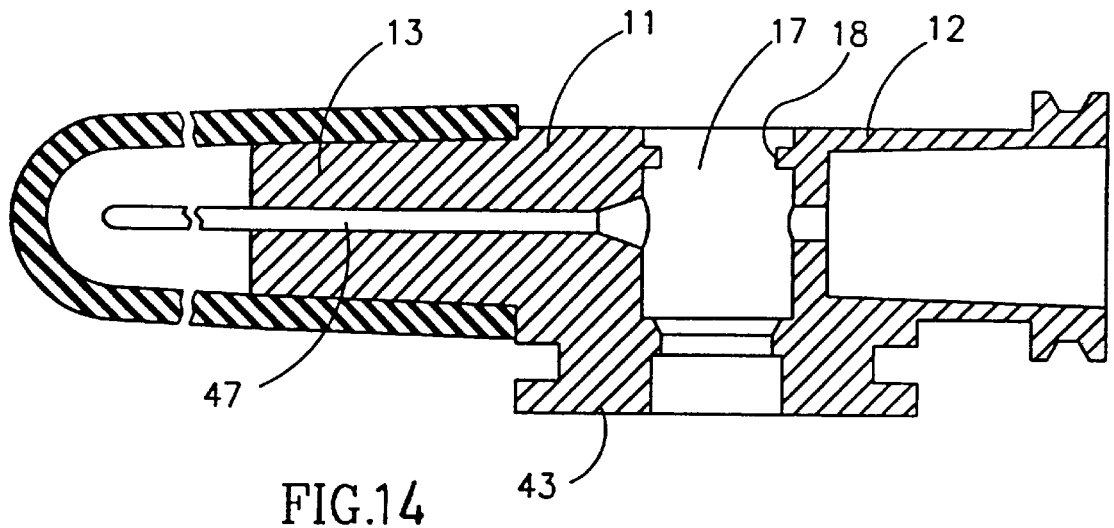
Figure 15:
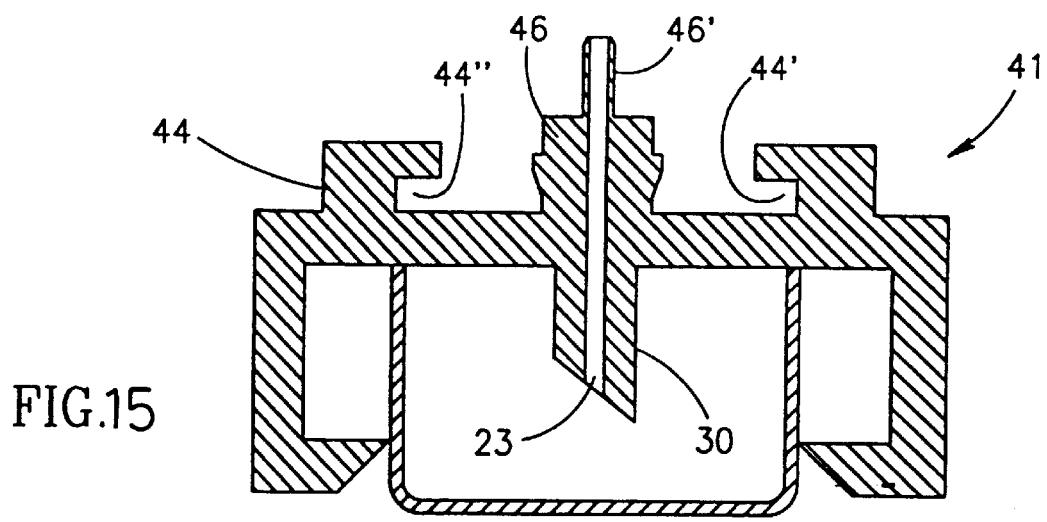
Figure 16:
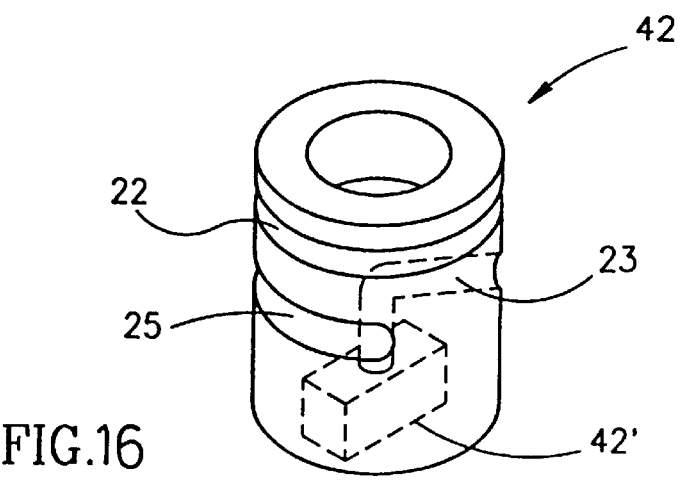
Figure 17A:
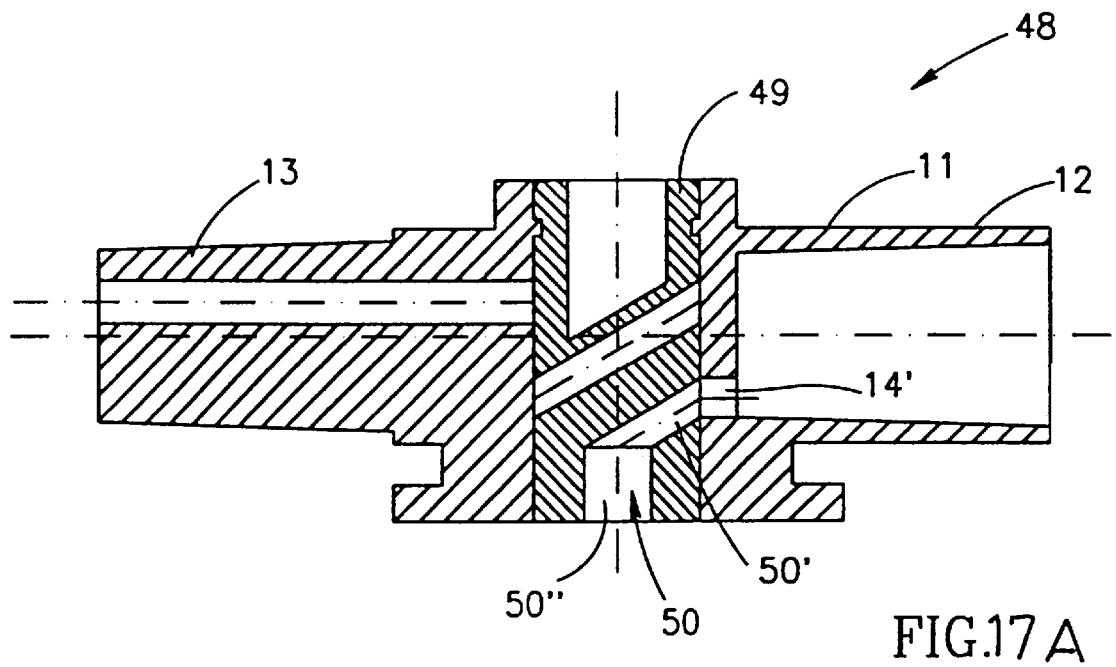
Figure 17B:
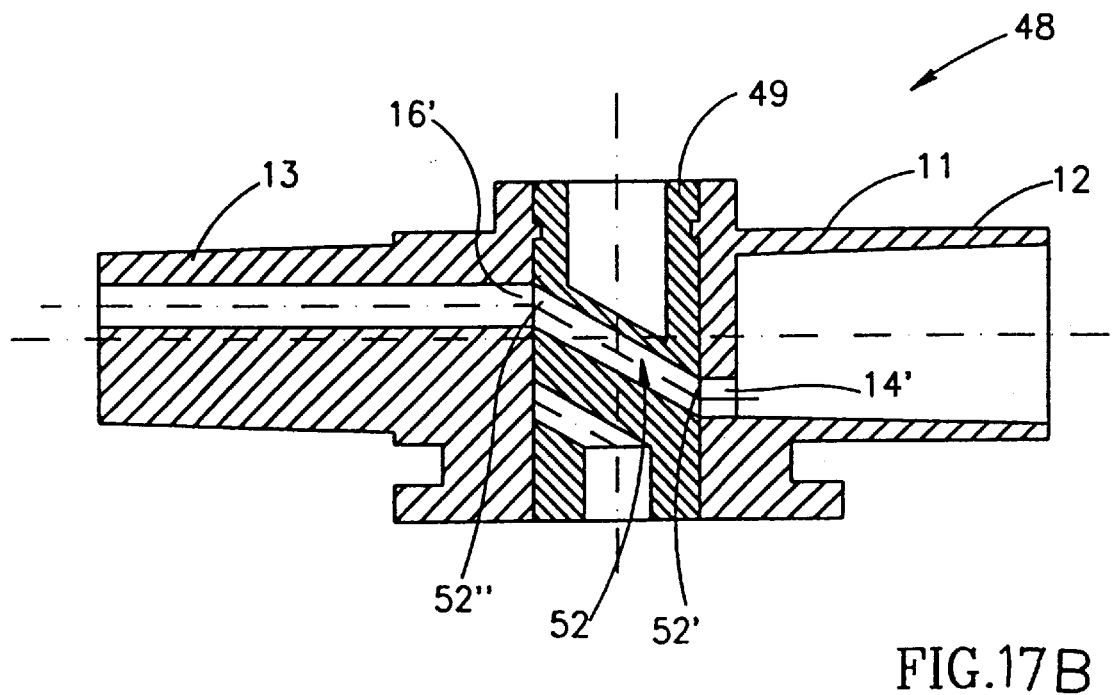
Figure 18:
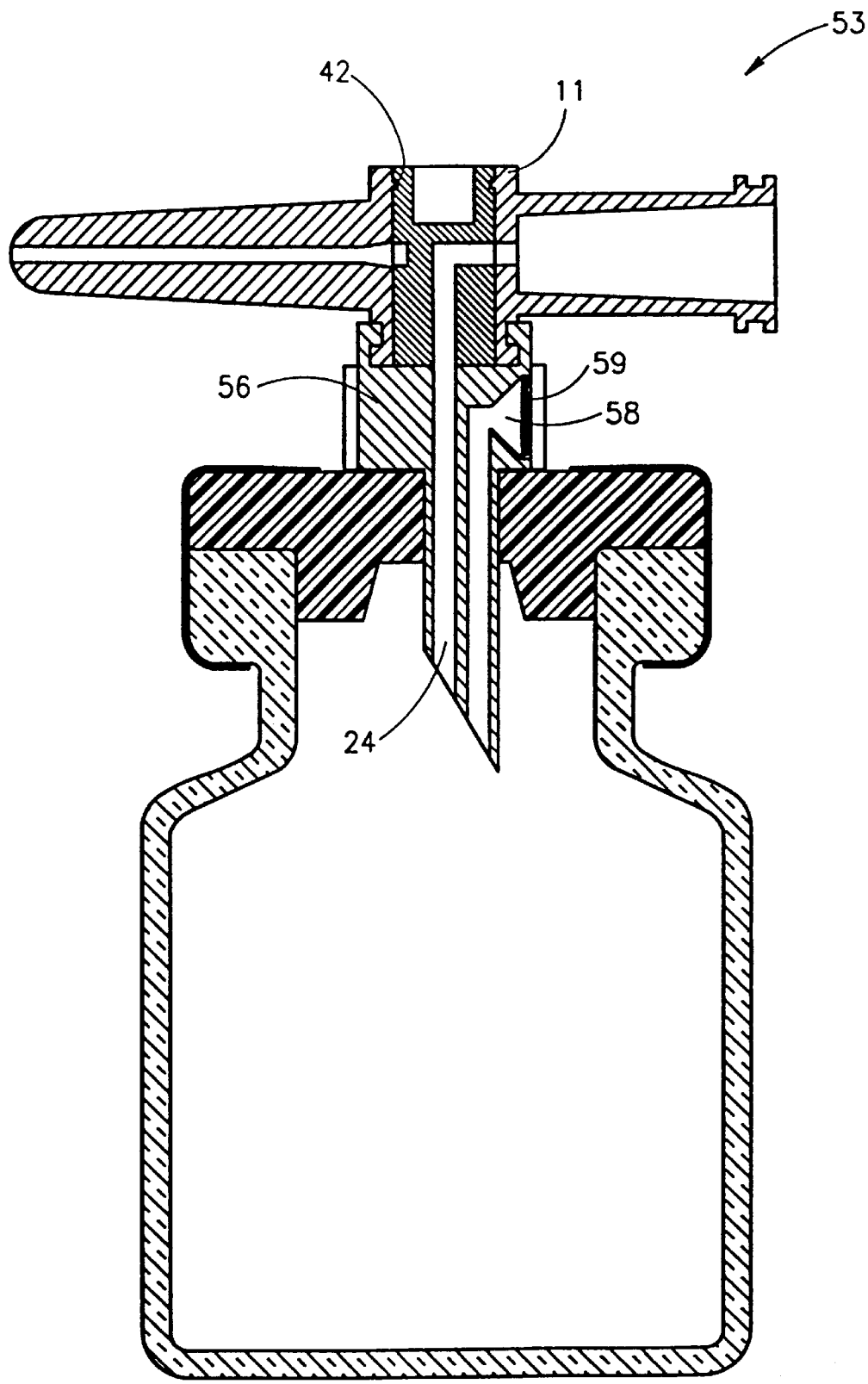
Figure 19A:
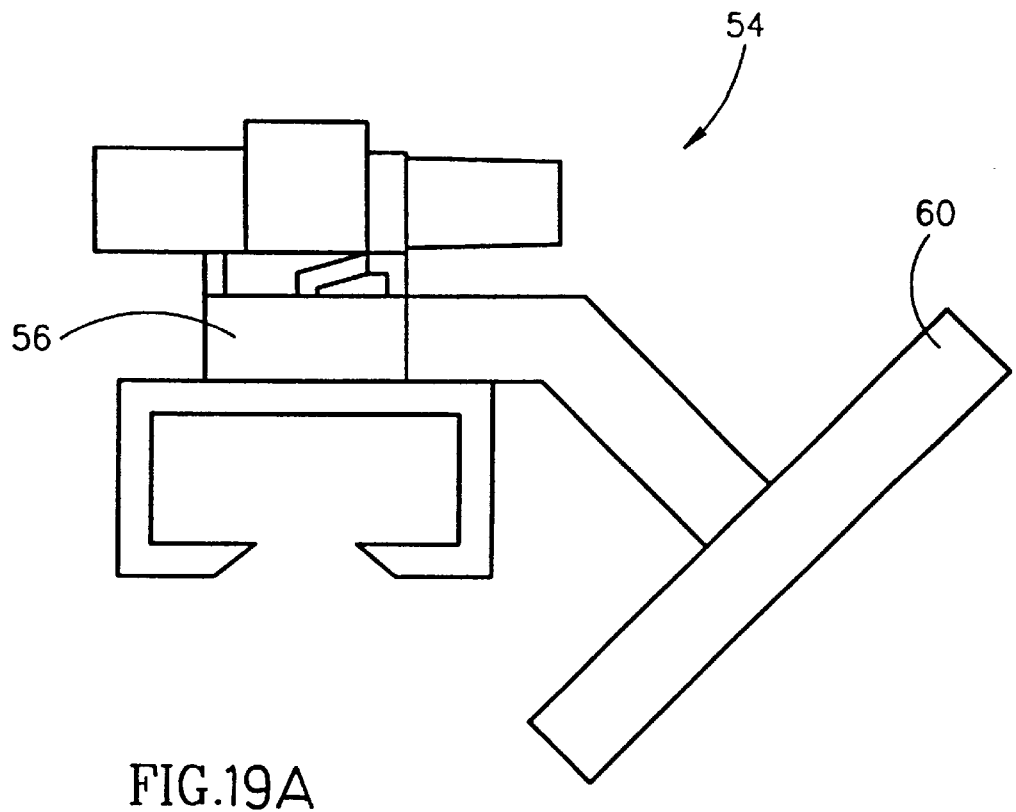
Figure 19B:
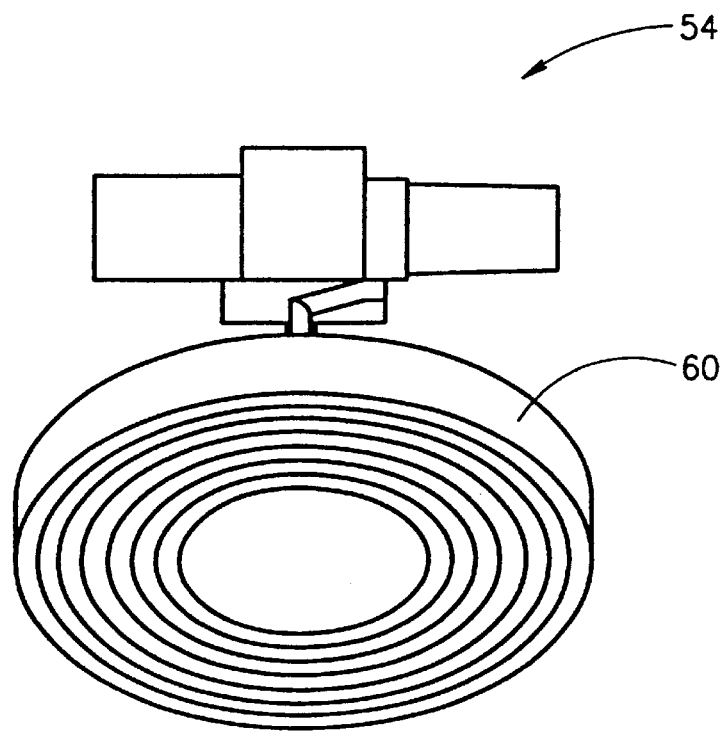
Figure 20:
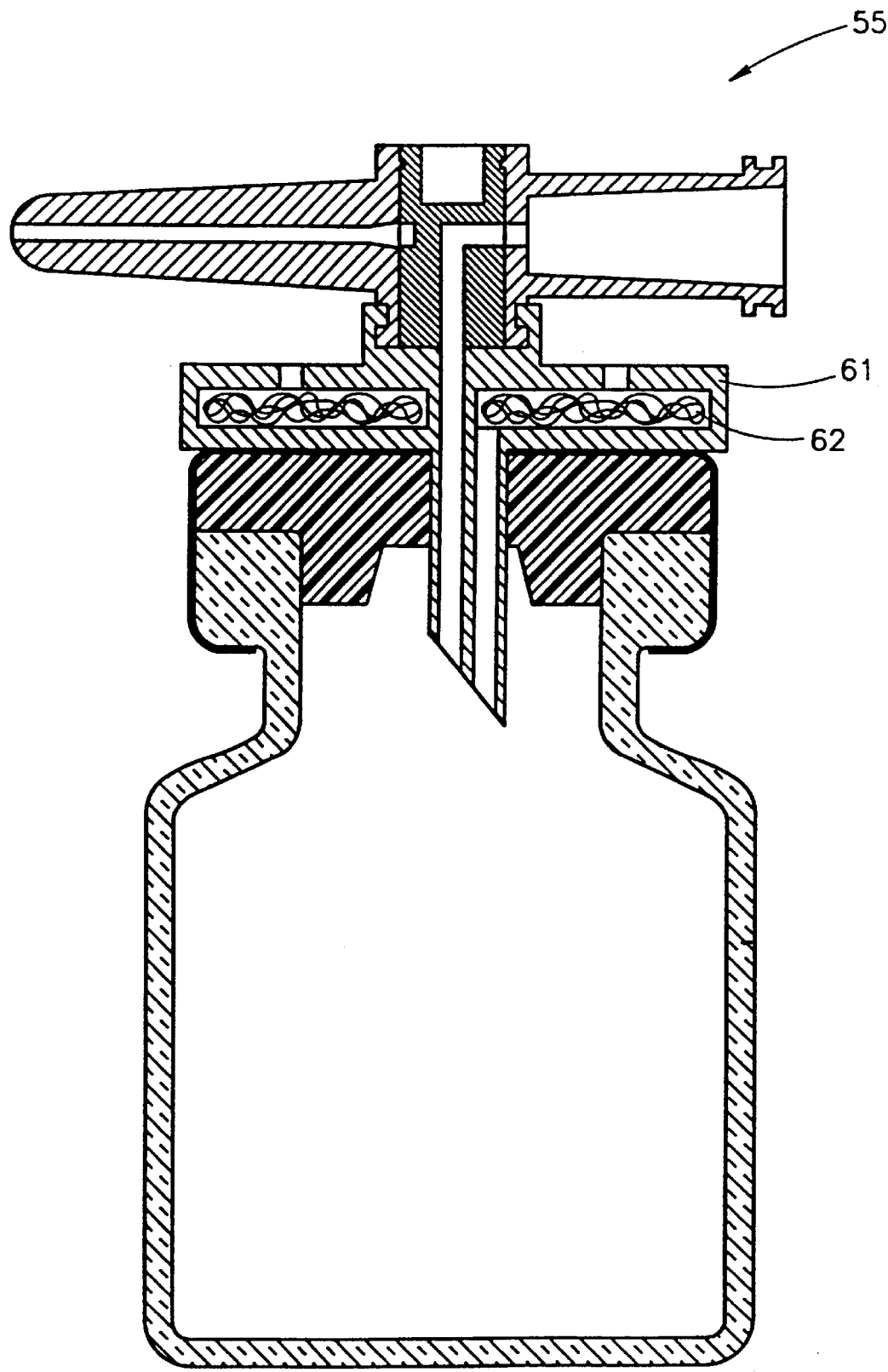
Figure 21:
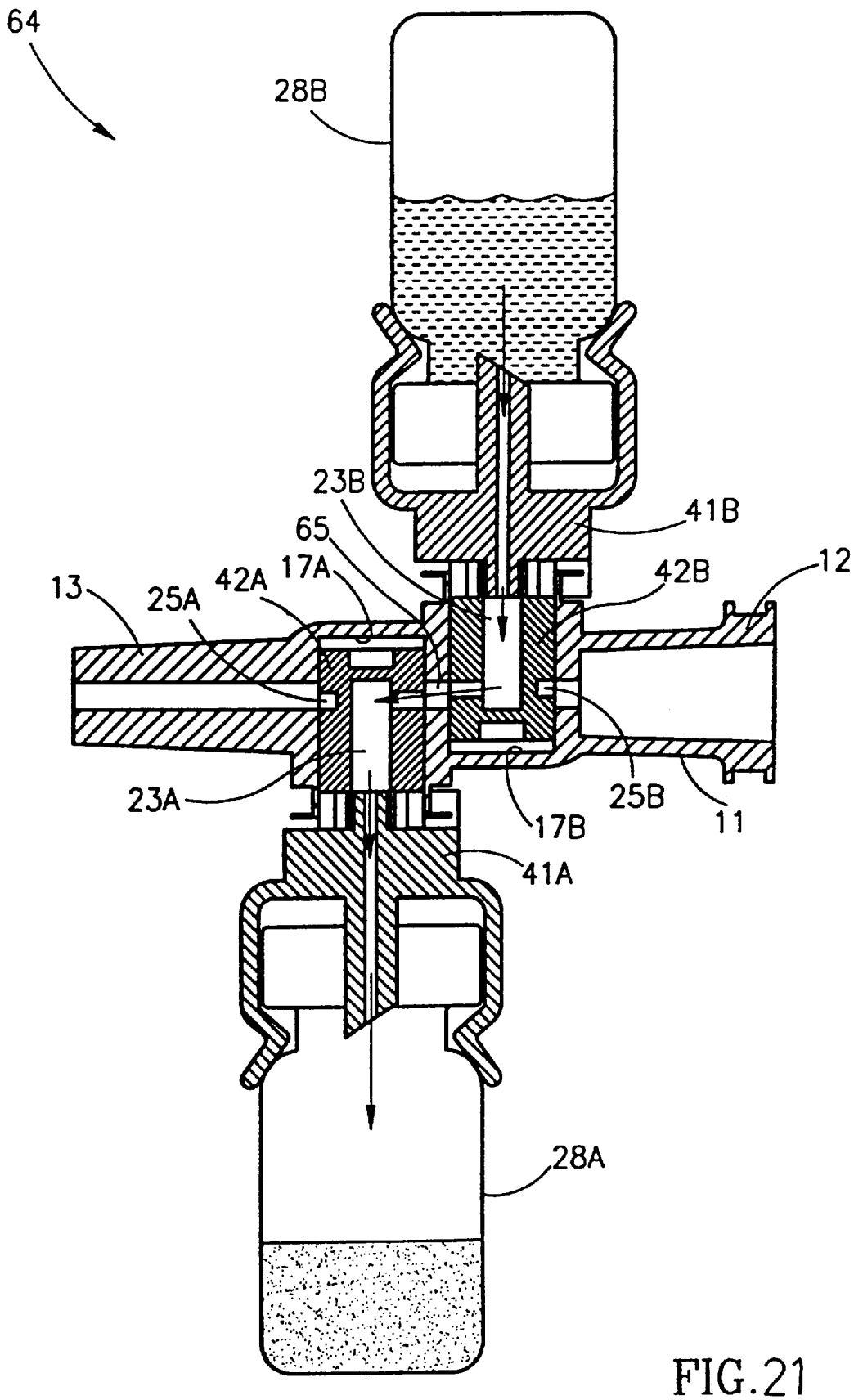
Figure 22:
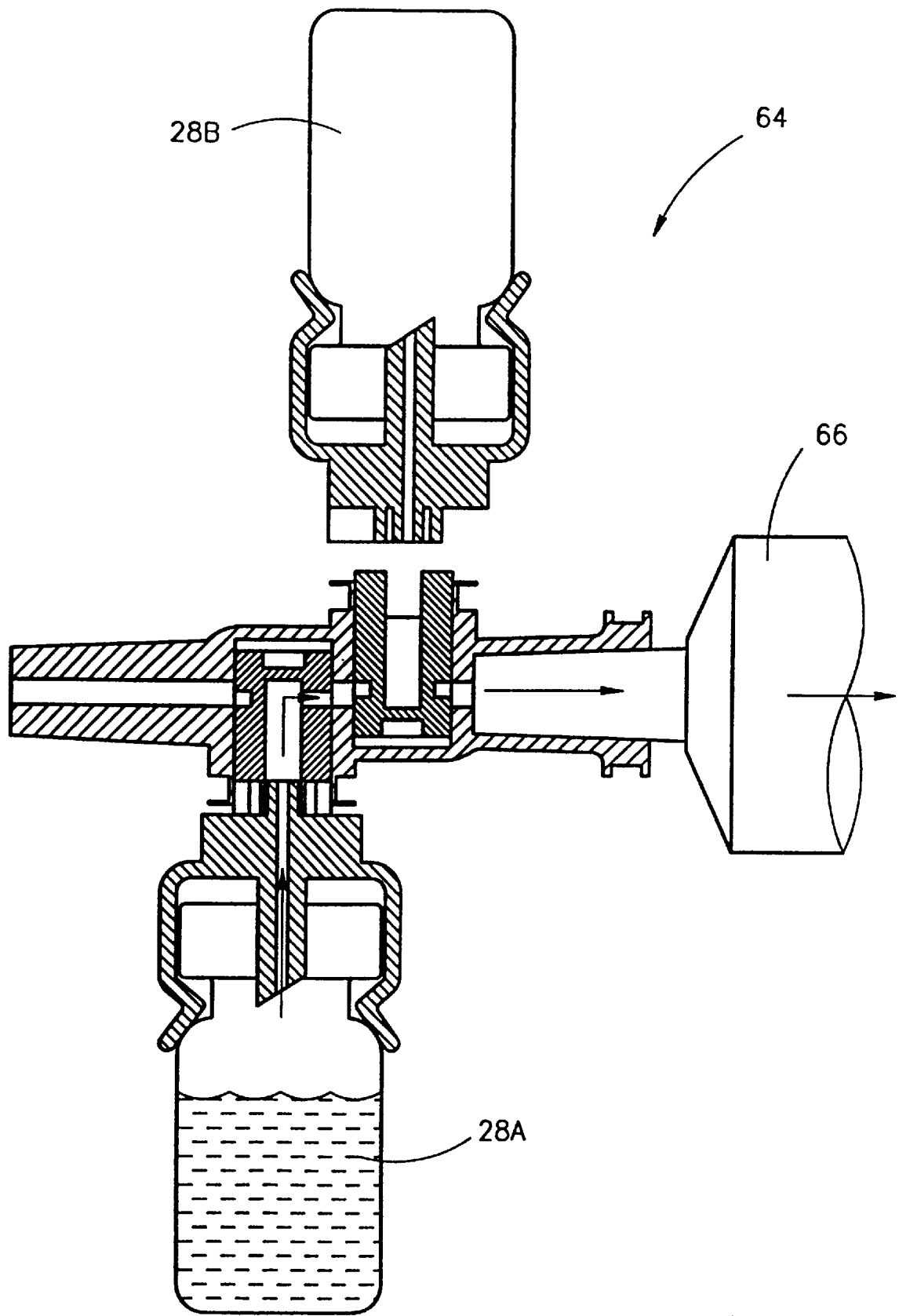
Figure 23:
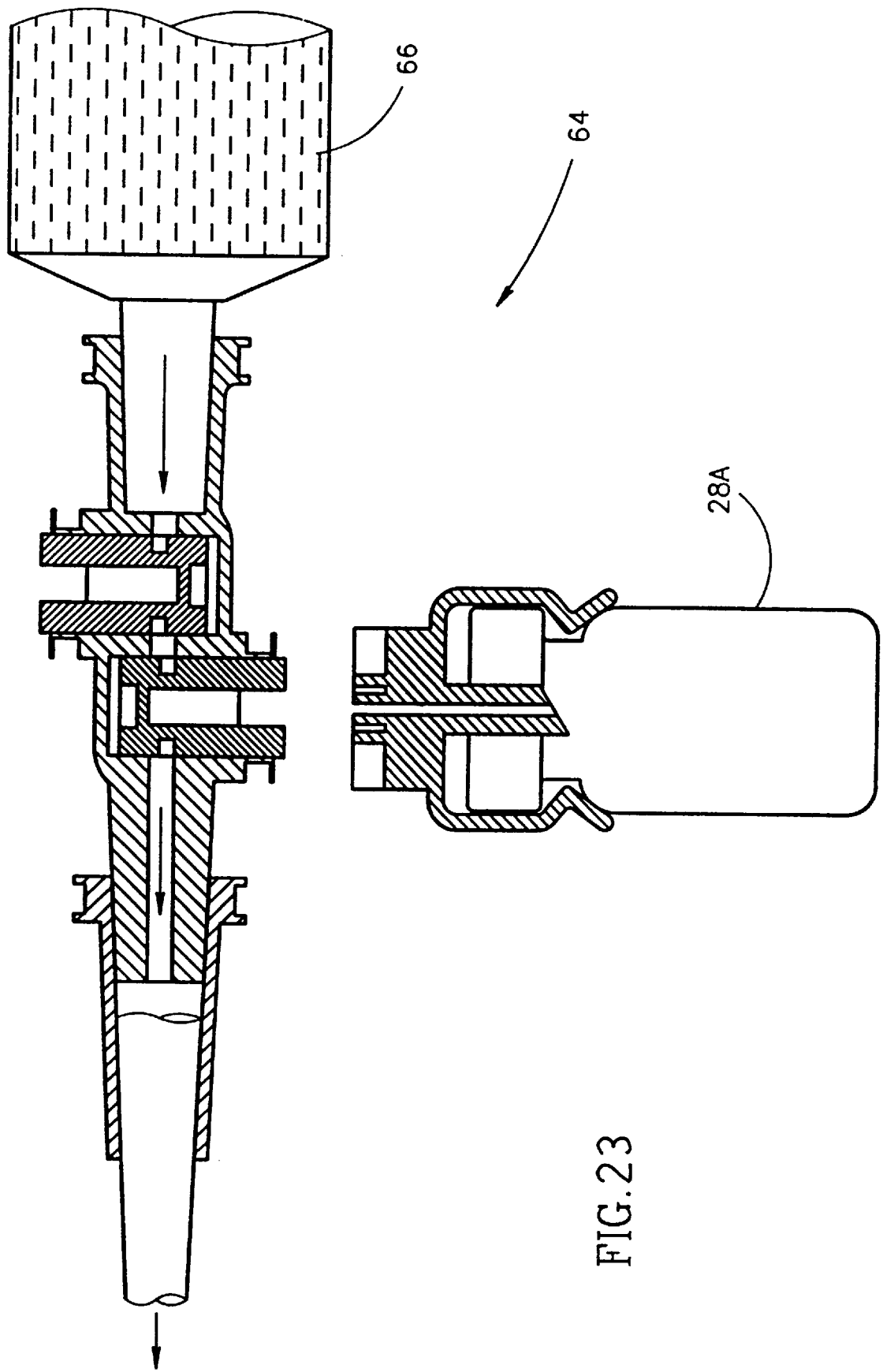
Figure 24:
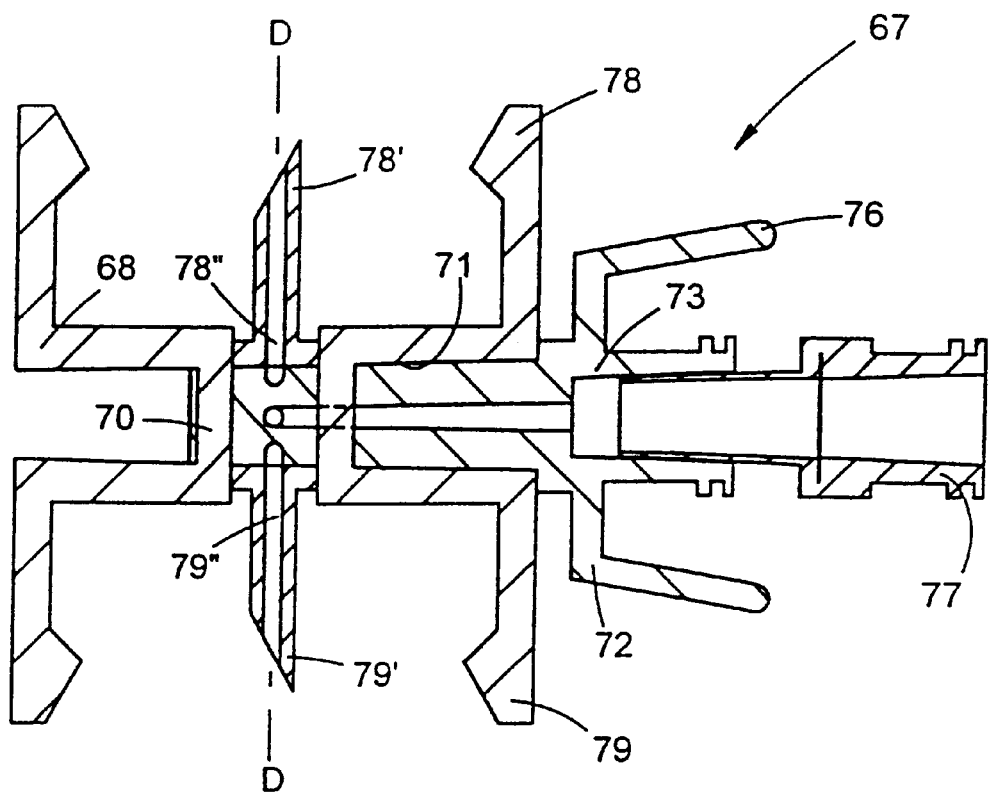
Figure 25:
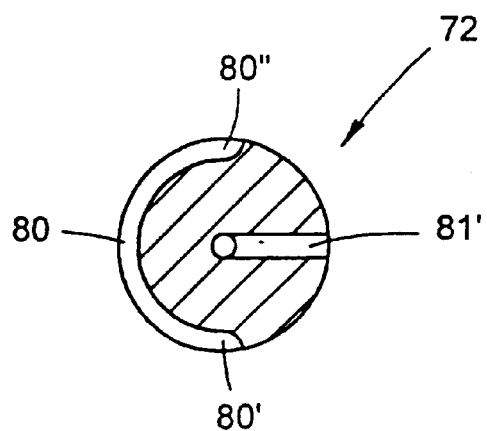
Figure 27:
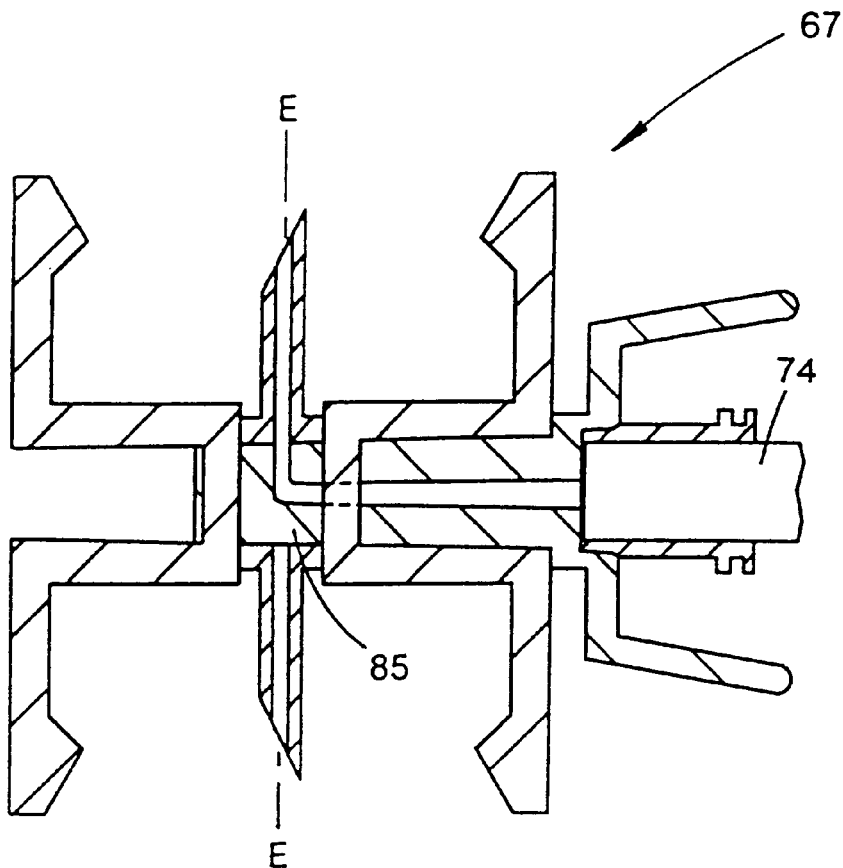
Figure 28:
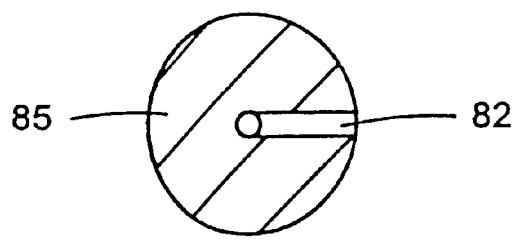
Figure 29:
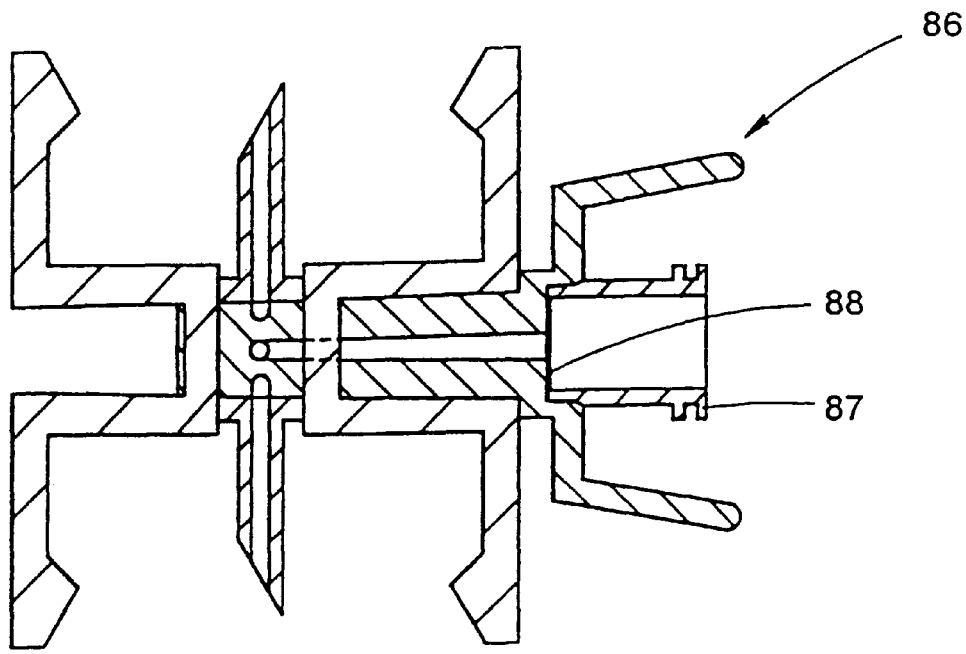
Figure 30:
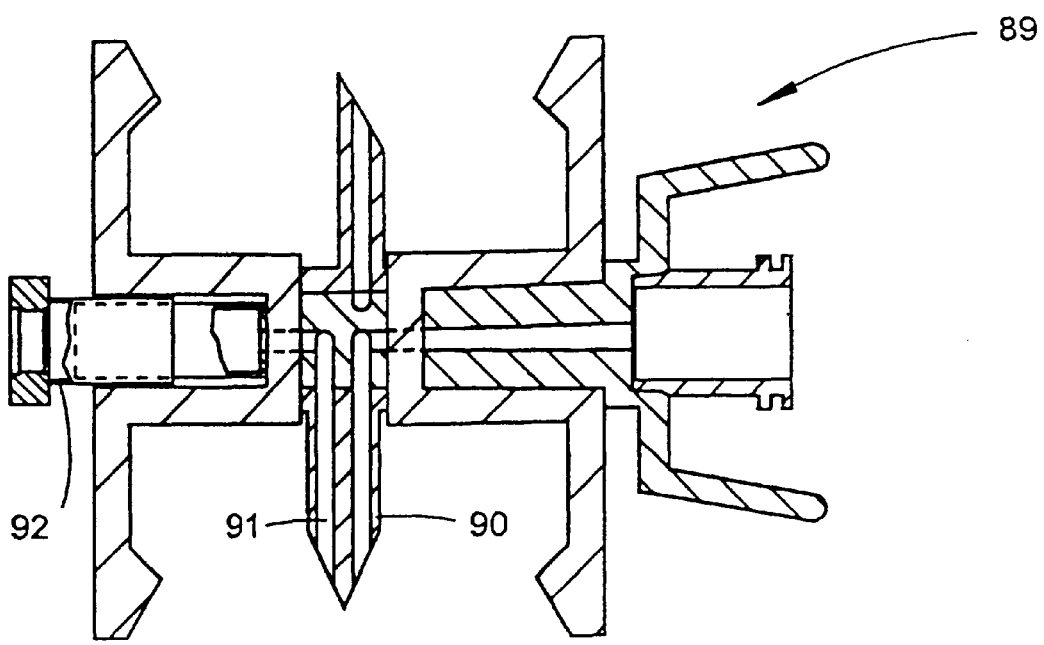

For a better understanding of the present invention and to show how the same may be carried out in practice, and solely by way of non-limiting examples, reference will now be made to the accompanying drawings, in which FIG. 1 is a top view of an applicator device for applying a two-component tissue glue according to the invention, FIG. 2 is a perspective view of an assembled fluid control device including a base member and an integrally formed adaptor cum flow control member for use with the applicator device according to FIG. 1, FIG. 3 is a perspective view of the fluid control device of FIG. 2 before assembly, FIG. 4 is a vertical cross sectional view of the fluid control device of FIG. 2 along the line A—A after insertion of a syringe of the applicator device of FIG. 1 and the attachment of a vial and before rotation of the adaptor relative to the base member, FIG. 5 is a horizontal cross sectional view of the fluid control device of FIG. 2 along the line B—B after insertion of a syringe of the application device of FIG. 1 and the attachment of a vial and before rotation of the adaptor relative to the base member, FIG. 6 is a horizontal cross sectional view of the fluid control device of FIG. 2 along the line C—C before rotation of the adaptor relative to the base member, FIG. 7 is a vertical cross sectional view of the fluid control device of FIG. 2 along the line A—A after rotation of the adaptor relative to the base member, FIG. 8 is a horizontal cross sectional view of the fluid control device of FIG. 2 along the line B—B after rotation of the adaptor relative to the base member, FIG. 9 is a horizontal cross sectional view of the fluid control device of FIG. 2 along the line C—C before rotation of the adaptor relative to the base member, FIG. 10 is a perspective view of a modified integrally formed adaptor cum flow control member adapted such that the adaptor breaks off from the flow control member on rotation of the adaptor relative to the base member beyond a pre-determined position, FIG. 11 is a perspective view of a fluid control device including the modified adaptor cum flow control member of FIG. 10 after the adaptor has been broken off, FIG. 12 is a perspective view of an assembled fluid control device including a base member and an adaptor designed for releasable engagement with the base member, FIG. 13 is a perspective view of the fluid control device of FIG. 12 after the adaptor has been rotated through a quarter turn ready for its detachment from the base member, FIG. 14 is a vertical cross sectional view of the base member of the fluid control device of FIG. 12, FIG. 15 is a vertical cross sectional view of the adaptor of the fluid control device of FIG. 12, FIG. 16 is a perspective view of the flow control member of the fluid control device of FIG. 12, FIGS. 17A and 17B are vertical cross sectional views of a fluid control device in which the flow control member is required to be rotated through 180° to enable switching between its flow control positions, FIG. 18 is a vertical cross sectional view of a fluid control device provided with an arrangement for the venting of a vial attached to its adaptor, FIGS. 19A and 19B are two views depicting a fluid control device having a filter for filtering air venting a vial attached to its adaptor, the filter being provided as a discrete element exterior to the device, FIG. 20 is a vertical cross sectional view of a fluid control device having an adaptor provided with a lateral cavity for receiving a filter for filtering air venting a vial attached thereto, FIG. 21 is a vertical cross-sectional view of a fluid control device in a first operative position enabling flow communication between a medicinal vessel containing a powder component and a medicinal vessel containing a physiological solution for enabling reconstitution of the powder component, FIG. 22 is a vertical cross sectional view of the fluid control device of FIG. 21 in a second operative position enabling flow communication between the vial containing the reconstituted component and a syringe of the applicator device of FIG. 1, FIG. 23 is a vertical cross sectional view of the fluid control device of FIG. 21 in a third operative position enabling flow communication between the syringe and the manifold of the applicator device of FIG. 1, FIG. 24 is a longitudinal cross sectional view of a fluid control device for use with a syringe and a pair of medicinal vessels of the applicator device of FIG. 1, FIG. 25 is a horizontal cross sectional view of the flow control member of the fluid control device of FIG. 24 along line D—D, FIG. 26 shows a series of steps (FIGS. 26A–26F) depicting the operation of the fluid control device of FIG. 24, FIG. 27 is a longitudinal cross sectional view of the fluid control device of FIG. 24 with a modified flow control member, FIG. 28 is a horizontal cross sectional view of the flow control member of FIG. 27 along line E—E in FIG. 27, FIG. 29 is a longitudinal cross sectional view of a modified fluid control device of FIG. 24 with an inline filter, and FIG. 30 is a longitudinal cross sectional view of a fluid control device with a modified adaptor enabling venting of a medicinal vessel attached thereto fitted with a hydrophobic filter.

FIG. 1 shows a plan view of an applicator device 110 for multi component tissue glues. Applicator device 110 comprises two supply containers provided as commercially available syringes 112 for solutions of proteins, such as fibrinogen, and of fibrinolytic substances, such as thrombin, of a two-component tissue glue. Each syringe 112 comprises a hollow cylindrical syringe body 114 having a front end 116 with an outlet opening 118 and connecting pieces 120, and an open rear end 122. Arranged in each syringe body 114 is a piston 124 in sealing abutment on the inner surface of syringe body 114. Piston 124 is held by a piston rod 126 guided out of syringe body 114 through the rear end 122. The piston rods 126 extend respectively in the longitudinal direction of the syringe bodies 114 (cf. the longitudinal axes 128 of the syringe bodies 114 indicated in the drawings). The free ends 130 of piston rods 126 facing away from piston 124 are have annular flanges 132 formed thereon. These annular flanges 132 are mechanically connected to each other by a connecting element 134. Connecting element 134 is formed with two receiving recesses 136 which are laterally open and suited for insertion of the annular flanges 132 thereinto.

As shown in the Figures, the two syringe bodies 114 are connected to each other by a clip holding means 138 (hereinbelow referred to as a holding element). Holding element 138 comprises two C-shaped holding clamps 140 of which the openings 142 are facing away from each other and which are connected to each other by their middle portions ("back portions"). Said openings 142 are oriented in the direction of the extension of that plane (here coinciding with the plane of FIG. 1) in which the longitudinal axes 128 of the syringe bodies 114 are arranged. Said clamps 140 are provided with two undergrip-projections 144. (In the view of FIG. 1, only one projection 144 is visible.) These projections 144 extend in mutually opposite directions, being arranged at a rotational displacement of 90° relatively to the two clamps 140 or respectively their openings 142. Thus, the two projections 144 respectively project at right angles from the plane (of FIG. 1) in which the longitudinal axes 128 of the syringe bodies 114 are arranged when the syringe bodies 114 are held by the holding element 138, or resp. in which the longitudinal axes of the clamps 140 extend, coinciding with the longitudinal axes 128 of the syringe bodies 114. This means that the projections 144 protrude in opposite directions along the axis of symmetry of the twin clamp arrangement.

The syringe bodies 114 are supported for sliding displacement on the holding element 138, because the resilient elastic holding clamps 140 extend by more than 180° and preferably by up to 200° around the syringe bodies 114 and thus enclose the syringe bodies 114 with a clamping force allowing for a relative displacement. The holding element 138 is arranged to bear on laterally protruding flanges 146 on the rear ends 122 of the syringe bodies 114, thus providing for a mutual abutment of holding element 138 and syringe body 114. The axial dimension of holding element 138 and especially of the holding clamps 140 is such that the scale markings arranged externally on the syringe bodies 114 are left unobstructed and are not covered by the holding element 138.

As evident from FIG. 1, the slightly conical connecting pieces 120 on the front ends 116 of the syringe bodies 114 are respectively connected to a fluid control device 148. Each fluid control device 148 is provided with a connector 150 receiving the conical connecting piece 120 of a syringe both 114. Each fluid control device 148 is provided with an outlet connecting piece 152 opposite to connector 150. Further, each fluid control device 148 is provided with a receiving adaptor 154 comprising a fluid conduit member 156. The receiving adaptor 154 is configured for insertion of a medicinal vessel thereinto, with the fluid conduit member, formed as a puncturing needle, penetrating the rubber closure plug of the vessel and extending into the interior of the vessel. Each fluid control device 148 has a floor control member (not shown in FIG. 1) rotatably supported therein. This flow control member can be rotated from outside, which is performed particularly by rotating the adaptor 154. By rotating the flow control member, the flow control member can be moved from a first fluid control position wherein a fluid path exists between a syringe body 114 and the medicinal vessel, into a second fluid control position wherein the syringe body 114 is in fluid connection with the outlet connecting piece 152 of fluid control device 148. The structure and the function of each fluid control device 148 will be explained in greater detail further below in connection with the preferred embodiments according to FIGS. 2 to 30.

The outlet connecting pieces 152 of fluid control device 148 have the connectors 158 of a connecting headpiece 160 mounted thereon. The connecting headpiece 160 is formed with channels 162 extending therethrough for connecting said connectors 158 to the outlet end 164 of connecting headpiece 160. Further, the connecting headpiece 160 is formed with an additional channel 166 extending therethrough and having a hose 168 for a medicinal gas, e.g. $O_2$, connected thereto. Also channel 166 extends to the outlet end 164 of connecting headpiece 160. On the outlet end 164, the connecting headpiece 160 is joined by a flexible three-lumen catheter 170, its three lumina being flush the inner channels 162 and 166 of connecting headpiece 160 at the outlet end 164 of headpiece 160.

Preferred embodiments of the fluid control device of applicator device 110 according to FIG. 1 will be explained in greater detail hereunder.

FIGS. 2 to 9 depict a first embodiment of a fluid control device, generally designated 10, for enabling fluid flow control between a syringe, a medicinal vessel and the manifold of the applicator device 110 of FIG. 1. The fluid control device 10 includes an elongated base member 11 having a port 12 adapted for receiving a syringe of the applicator device 110 and a dispensing port 13 fashioned as a plastic cannula for insertion into the manifold of the applicator device 110. The port 12 is typically fashioned as a female Luer connector.

As shown in FIG. 4, the port 12 includes a lumen 14 having an interior opening 14' and the dispensing port 13 includes a lumen 16 having an interior opening 16'. The lumenina 14 and 16 are co-axial and in flow communication via a bore 17 transversely disposed relative to the elongated base member 11. The bore 17 includes an upper peripheral flange 18 and a lower minor peripheral abutment wall portion 19' protruding radially inward relative to its major peripheral wall portion 19" (see FIG. 6). As shown, the abutment wall portion 19' typically extends through an arc angle of about 90°.

The fluid control device 10 further includes an integrally formed adaptor cum flow control member, generally designated 20, for insertion into the bore 17 wherein it is restrained by means of a peripherally formed groove 22 designed for receiving the flange 18 therein. The flow control member 20' is formed with two flow ducts as follows: a first flow duct 23 (see FIG. 4) in the form of an L-shaped channel having a radial aperture 23' for registration with the interior opening 14' and an axial aperture 23' of a fluid conduit member 24 integrally formed as part of the adaptor 20" on disposition of the flow control member 20' in a first flow control position enabling flow communication between a syringe inserted in the port 12 and a vessel attached to the adaptor 20"; a second flow duct 25 (see FIG. 5) in the form of a peripheral slightly longer than a semi-circular groove 25 having a first end portion 25' for registration with one of the interior openings 14' and 16' and a second end portion 25" for registration with the other of the interior openings 14' and 16' on disposition of the flow control member 20' in a second flow control position enabling flow communication between a syringe inserted in the port 12 and the dispensing port 13.

In addition, the flow control member 20' is provided with a minor peripheral abutment wall portion 26' protruding radially outward relative to its major peripheral wall portion 26" (see FIG. 6). As shown, the abutment wall portion 26' typically extends through an arc angle of about 90°. The minor peripheral abutment wall portions 19' and 26' are so disposed such that they assume substantially diagonally opposing positions relatively to one another (see FIG. 6) in the first flow control position of the flow control member 20'.

The adaptor 20" is shown to be adapted for the attachment thereto of a vial 28 (not drawn to size) provided with a rubber stopper 29. As such, the fluid conduit member 24 is fashioned as a puncturing tool 30 for penetrating a rubber stopper 29 on attachment of a vial 28 to its adaptor 20". Alternatively, the adaptor 20" can be adapted for the attachment thereto of an ampoule 31 (not drawn to size), the difference being that such an adaptor will preferably have relatively long springy grips.

Each stage of the two stage operation of the fluid control device 10 for the filling of the syringe bodies with tissue glue components provided in powder form for dilution with a physiological solution provided in a pre-filled syringe is now described with reference to FIGS. 4 to 6 and FIGS. 7 to 9, respectively.

As shown in FIGS. 4 to 6, the fluid control device 10 is best provided in a set-up position in which the flow control member 20' is in its first flow control position and the two minor abutment wall portions 19' and 26' are diagonally opposed to one another. As shown, it should be noted as best seen in FIG. 5, that the semi-circular groove 25 registers with the interior opening 16' but does not provide a flow path.

In this arrangement, a pre-filled syringe 32 is inserted into the port 12 and the vial 28 is attached to the adaptor 20" by means of which action, the puncturing tool 30 punctures the vial's rubber stopper 29, thereby enabling flow communication with its interior via the fluid conduit member 24. Typically, the syringe 32 requires actuation for expressing its contents into the vial 28 whilst, in some cases, if the contents of the vial 28 are under vacuum, then the physiological solution of the syringe 32 can be sucked into the vial without user intervention. Thereafter, the contents of the vial 28 are shaken so as to reconstitute the powdered tissue glue component. The fluid control device 10 together with the vial 28 are then preferably inverted and the syringe 32 is aspirated so as to draw the reconstituted liquid tissue glue component thereinto.

Turning now to FIGS. 7 to 9, the vial 28 together with the adaptor 20" are rotated in either a clockwise or a counter clockwise direction relative to the base member 11 until such time that abutment wall portion 26' is stopped by the abutment wall portion 19' (see FIG. 9). On rotation of the adaptor 20", the flow control member 20' is rotated to its second flow control position enabling a flow path between the syringe 32 and the dispensing port 13 by means of the end portions 25' and 25" of the semi-circular groove 25 registering with the interior openings 14' and 16'. The tissue glue component can then be dispensed by actuation of the syringe 32.

As is readily appreciated now, the fluid control device 10 ensures that the filling of the syringe body of the tissue glue applicator device 110 of FIG. 1 with the tissue glue component is performed under aseptic conditions.

FIGS. 10 and 11 depict a second embodiment of a fluid control device, generally designated 34, constructed and operative in accordance with the teachings of the present invention for enabling fluid flow control between a syringe, a medicinal vessel and a dispensing port. The fluid control device 34 is similar in construction and operation to the fluid control device 10 and therefore the same reference numbers are used where appropriate.

The main difference between the two fluid control devices 34 and 10 resides in the fact that the former includes an integrally formed adaptor cum flow control member 35 provided with a weakened portion, generally designated 36, between its abutment wall portion 26' of its flow control member 35' and its adaptor 35". As shown, this weakened portion 36 is achieved by leaving radially extending vanes 36' formed by cut-outs 36".

The advantage of this design is that after rotation of the vial 28 (not shown) and the adaptor 35" through 90° so as to rotate the flow control member 35' from its first flow control position to its second flow control position, any further torque applied will tend to snap off the adaptor 35" which can then be discarded together with the vial, thereby rendering a less cumbersome and lighter remaining assembly of the tissue glue applicator device 110 of FIG. 1 so as to facilitate the application of a tissue glue.

A further difference between the fluid control devices 34 and 10 resides in the fact the former includes a dispensing port 38 fashioned as a male Luer connector.

FIGS. 14 to 16 depict a third embodiment of a fluid control device, generally designated 40, constructed and operative in accordance with the teachings of the present invention for enabling fluid flow control between a syringe, a medicinal vessel and a dispensing port. The fluid control device 40 is similar in construction and operation to the fluid control device 10 and therefore the same reference numerals are used where appropriate.

The main difference between the two fluid control devices 40 and 10 resides in the fact that the former includes an adaptor 41 designed for a non-destructive detachable engagement with a flow control member 42. As such, the base member 11 is provided with a downwardly depending rectangular shaped skirt 43 provided with outwardly extending flanges 43' and 43" for engagement by an upwardly extending rectangular shaped grip 44 of the adaptor 41 provided with inwardly directed grooves 44' and 44" for receiving the flanges 43' and 43". In addition, the adaptor 41 is provided with an upwardly extending stem 46 provided with a rectangular shaped key 46' for insertion into a similarly sized and shaped slot 42' formed in the underside of the flow control member 42.

In the fluid control device 40, the flow control member 42 is disposed in its first flow control position enabling a flow path between the port 12 and a medicinal vessel to be attached to the adaptor 41 when the adaptor 41 is mounted on the base member 11. Conversely, on the rotation of the adaptor 41 relative to the base member 11 to a position enabling axial detachment therefrom, the adaptor 41 urges the flow control member 42 from its flow control position to its second flow control position enabling a flow path between the port 12 and the dispensing port 13. Preferably, there is a screw thread engagement between the base member 11 and the adaptor 41 designed such that there is an axial displacement of the adaptor 41 away from the base member 11 when it is rotated from its engaging position to its disengaging position.

It can be readily appreciated that the advantage of this design over the design of the fluid control device 34 whilst retaining all the advantages of the latter resides in the fact that the former is reusable after sterilization whilst the latter can only be used once due to the destruction of the adaptor cum flow control member 35.

A further difference between the fluid control devices 40 and 10 resides in the fact the former includes a dispensing port 13 provided with a needle 47.

FIGS. 17A and 17B depict a fourth embodiment of a fluid control device, generally designated 48, constructed and operative in accordance with the teachings of the present invention for enabling fluid flow control between a syringe, a medicinal vessel and a dispensing port. The fluid control device 48 is similar in construction and operation to the fluid control device 41 and therefore the same reference numerals are used where appropriate.

The main difference between the two fluid control devices 48 and 41 resides in the fact that the former includes a flow control member 49 which is required to be rotated through a 180° turn between its first flow control position (see FIG. 17A) and its second flow control position (see FIG. 17B). In particular, the flow control member 49 includes an inclined channel 50 having a radial aperture 50' for registration with the interior opening 14' and an axial aperture 50" for registration with the fluid conduit member 24 so as to enable the flow path between a syringe and the interior of a medicinal vessel. And, the flow control member 49 includes a second inclined channel 52 having a radial aperture 52' for registration with the interior opening 14' and a radial aperture 52" for registration with the interior opening 16' so as to enable the flow path between the syringe to the dispensing port 13. As shown, in this case, the lumina 14 and 16 are not co-axial.

FIGS. 17 to 20 depict other modified fluid control devices, generally designated 53, 54 and 55 constructed and operative in accordance with the teachings of the present invention for enabling fluid flow control between a syringe, a medicinal vessel and a dispensing port. The fluid control devices 53, 54 and 55 are similar in construction and operation to the fluid control device 41 and therefore the same reference numerals are used where appropriate. The main difference between the fluid control devices 53, 54 and 55 and the fluid control device 41 is that they provide arrangements for venting a vial and, if necessary, for filtering incoming air.

Turning now to FIG. 18, the fluid control device 53 includes an adaptor 56 provided with a venting conduit 58 for venting a vial 28 to the atmosphere in addition to the fluid conduit member 24. The venting conduit 58 is preferably provided with a filter 59 for filtering incoming air. Turning now to FIGS. 19a and 19b, the fluid control device 54 is similar to the fluid control device 53 except that it includes a filter 60 exterior to the adaptor 56. Turning now to FIG. 20, the fluid control device 55 is similar to the fluid control device 53 except that its adaptor 61 includes an integrally formed laterally disposed filter 62.

FIGS. 21 to 23 depict a fluid control device, generally designated 64, for enabling the reconstitution of a powdered tissue glue component with a physiological solution contained in a medicinal vessel instead of within a prefilled syringe as required with the fluid control device 10. The fluid control device 64 is similar in construction and operation to the fluid control device 41 and therefore the same reference numerals are used where appropriate.

The main difference between the two fluid control devices 64 and 41 resides in the fact that the former is adapted to be fitted with two medicinal vessels and, as such, its base member 11 is provided with a port 12, a dispensing port 13 and two bores 17A and 17B which are interconnected by a channel 65. As shown, the medicinal vessels are vials 28A and 28B where the vial 28A contains a powdered tissue glue component and the vial 28B contains the physiological solution for diluting the powdered tissue glue component. As explained in greater detail hereinbelow for the case when the vial 28A has its contents under a high vacuum, the sequence and order of the attachment of the vials 28A and 28B to the adaptors 41A and 41B is not arbitrary.

In this case, the flow control member 42A has a first flow control position in which its L-shaped flow duct 23A registers in flow communication with the channel 65 and a medicinal vessel attached to its adaptor 41A (see FIGS. 21 and 22) and a second flow control position in which its peripheral groove flow duct 25A registers in flow communication with the channel 65 and the dispensing port 13 (see FIG. 23). In contrast, the flow control member 42B has a first flow control position in which its L-shaped flow duct 23B registers in flow communication with the channel 65 and a medicinal vessel attached to its adaptor 41B (see FIG. 21) and a second flow control position in which its peripheral groove flow duct 25B registers in flow communication with the channel 65 and the port 12 (see FIGS. 22 and 23).

The operation of the fluid control device 64 for the filling of a syringe body of the applicator device 110 of FIG. 1 with a powdered tissue glue component provided in the pressurized vial 28A after constitution with a physiological solution provided in the vial 28B is now described. First, as shown in FIG. 21, the fluid control device 64 is provided in its first operative position, namely, enabling the flow path between the vials 28A and 28B when they are attached to the base member 11. It should be noted that the vial 28B is attached to the adaptor 41B and thereafter the pressurized vial 28A is attached to the adaptor 41A such that the physiological solution contents of the vial 41B is sucked into the vial 28A. Reconstitution typically requires shaking the fluid control device 64. As shown in FIG. 22, the adaptor 41B together with the vial 28B are then rotated so as to enable their detachment from the base member 11 whilst, at the same time, effecting the rotation of the flow control member 42B so as to enable a flow path between the port 12 and the remaining vial 28A. A syringe 66 is inserted into the port 12 and, after inversion of the fluid control device 64 such that the vial 28 containing the reconstituted tissue glue component assumes an upward position, the syringe 66 is aspirated to draw the contents of the vial 28A thereinto. Thereafter, as shown in FIG. 23, the adaptor 41A together with the vial 28A are rotated so as to enable their detachment from the base member 11 while, at the same time, effecting the rotation of the flow control member 42A so as to enable a flow path between the syringe 66 and the dispensing port 13. Finally, in this position, the syringe 66 is actuated so as to express the respective tissue glue component for its application along with another component to an application site via the dispensing port 13.

FIGS. 24 to 26 depicts a fluid control device 67 allowing the preparation of a tissue glue component by the mixing between a first substance contained in a first medicinal vessel and a second substance contained in a second medicinal vessel and thereafter the transfer of the tissue glue component to a dispensing tool, namely, a syringe. The fluid control device 67 includes a base member 68 having a generally tubular intermediate portion 70 defining a lumen 71 in which a flow control member 72 is rotatably inserted. The flow control member 72 has a port 73 for receiving a dispensing tool, typically, a syringe 74 (see FIG. 26). The port 73 is preferably fashioned as a female Luer connector. The flow control member 72 also has integrally formed handles 76 for enabling a manual rotating thereof. As shown, a filter 77 can also be deployed within the port 73 for filtering a tissue glue component on its aspiration into a syringe 74.

The base member 68 includes two adaptors 78 and 79 which are suited for the attachment thereto of medicinal vessels. In this case, the adaptors 78 and 79 are suited for the attachment thereto of vials and, as such, they include respective co-axial fluid conduit members 78' and 79' fashioned as piercing tools for puncturing the vials' rubber stoppers. The fluid conduit members 78' and 79' have respective internal apertures 78" and 79".

The flow control member 72 is rotatably mounted for enabling either, in a first flow control position, a flow path between vials attached to the adaptors 78 and 79 or, in a second flow control position, a flow path between the syringe and one of the vials. As such, in a similar manner to the flow control member 20' (see FIGS. 3 and 5), flow control member 72 includes two flow ducts as follows: A first flow duct 80 in the form of a peripheral groove slightly longer than semi-circular having end portions 80' and 80" for registration with the interior apertures 78" and 79" so as to enable a flow path between the interiors of vials when attached to the adaptors 78 and 79. And a second flow duct 82 in the form of an L-shaped channel having a radial aperture 82' for registration with the interior opening 72' and an axial outlet port 82" so as to enable a flow path between a vial attached to one of the adaptors 78 and 79 and a syringe inserted in the port 77.

The operation of the fluid control device 67 is now described with reference to the steps depicted in FIG. 26 for the case that a vial 83 contains a dried tissue glue component, e.g. a powder, a crystalline material, a lyophilizate, etc., stored under a high vacuum and a vial 84 contains a physiological solution. As explained in greater detail hereinbelow for the case when the vial 83 has its contents under a high vacuum, the sequence of attachment of the vials 83 and 84 to the adaptors 78 and 79 is not arbitrary.

The fluid control decide 67 is typically provided in a hermetically sealed package with its flow control member 72 set so as to enable the flow path between flow conduit members 78' and 79' by means of the ends 80' and 80" of its semi-circular groove 80 registering with their interior openings 78" and 79" (FIG. 26A). The vial 84 containing the diluent solution is attached to the adaptor 78 (FIG. 26B), the action of attachment puncturing its rubber stopper and thereafter the vial 83 containing the dried tissue glue component is attached to the adaptor 79 (FIG. 26C) thereby sucking the diluent solution thereinto once its rubber stopper is punctured (FIG. 26D). The contents of the vial 83 are then shaken so as to mix the diluent solution with the dried tissue glue component.

The syringe 74 is inserted into the port 73 (FIG. 26D) and the flow control member 72 is rotated through a quarter turn relative to the base member 11 such that the flow path between the syringe 74 and the vial 83 is enabled (FIG. 26E). The fluid control device 67 is then inverted (FIG. 26F) and the syringe 74 is aspirated so as to draw the reconstituted tissue glue component thereinto, the medicinal preparation passing through a deployed filter 77, if any, thereby becoming particle free for application to an application site.

FIGS. 27 and. 28 depict the fluid control decide 67 with a modified flow control member 85 having just the L-shaped flow duct 82, thereby requiring that it be rotated through a 180° turn for switching between its two flow control positions, the first flow control position being between a syringe inserted in the port 73 and a first medicinal vessel whilst the second flow control position being between a syringe inserted in the port 73 and a second medicinal vessel.

The difference between the flow control member 85 and 72 being that a fluid control device 67 fitted with the former can be employed with medicinal vessels in which their contents are under a low vacuum or no vacuum, thereby requiring user intervention to perform the mixing of the powdered tissue glue component with the physiological solution. In particular, the flow control member 85 is suitable for use with a fluid control decide 67 having an adaptor suitable for connection to an IV bag such that on setting the flow control member 85 in its first operative position, the syringe 74 is aspirated so as to introduce a predetermined volume of diluent solution thereinto. Thereafter, on setting the flow control member 85 into its second operative position, the syringe 74 is actuated so as to introduce the diluent solution into a second medicinal vessel containing the tissue glue component to be reconstituted. After mixing of the tissue glue component with the diluent solution, the syringe 74 is aspirated a second time so as to introduce the medicinal liquid thereinto at which time the syringe 74 is removed for application of the tissue glue component to an application site. In this fashion, such a fluid control device can be used a number of times with one or more medicinal vessels.

FIG. 29 depicts a fluid control device 86 with a port 87 provided with an integral in-line filter 88, thereby obviating the need for a filter 77. FIG. 30 depicts a fluid control device 89 with a modified adaptor 90 having a vent conduit 91 for venting the vial attached thereto provided with a hydrophobic filter 92 so as to prevent wastage of the mixed tissue glue component when the fluid control device 89 is manipulated into the position shown in FIG. 26F.

The use of the different embodiments of the fluid control device 148 of the applicator device 110 described above with reference to FIGS. 2 to 30 offers the advantage that the applicator device can be filled with the glue components in an easy and uncomplicated manner. For this filling process, applicator device 110 is used in the configuration shown in FIG. 1, i.e. in the condition suited for applying the tissue glue. The two medicinal vessels containing the components need only be mounted to the adaptors 154. Subsequently, the two piston rods 126 are actuated by pulling the connecting element 134 so that the contents of the medicinal vessel is sucked into the syringe bodies 114. At this point of time, the flow control members of both fluid control devices 148 are arranged in that fluid control position in which the puncturing needles 156 are connected to the syringe bodies 114.

After the syringe bodies 114 have been filled, the adaptors 154 are rotated whereby also the flow control members are rotated at the same time so that the syringe bodies 114 are now connected to the manifold. After being rotated, the adaptors 154 are taken off the fluid control devises 148. Thus, the relatively large-sized adaptors 154 will not disturb the application of the tissue glue. The tissue glue can now be applied without further manipulation of the applicator device.

We claim:

1. An applicator device for applying a multi component fluid, especially a multi component tissue glue, comprising
   a plurality of substantially cylindrical supply containers for respectively one component of the fluid to be applied, each of said supply containers having a front end with an opening for dispensing the fluid component from the supply container, a rear end facing away from the front end, and a slideably displaceable piston having a piston rod extending out of said rear end for operating the piston, and
   a connecting headpiece provided with connectors for fluid connection with the front ends of the supply containers, said connecting headpiece having channels for the individual components of the fluid to be applied extending therethrough from said connectors of the connecting headpiece to an outlet end,
characterized in
   that a fluid control device is arranged in at least one of said fluid connections between the front ends of the supply containers and the connectors of the connecting headpiece, said fluid control device comprising
      a first port connected to a connector of the connecting headpiece,
      a second port connected to the front end of a supply container,
      a third port connectable to a medicinal vessel, said third port comprising an adaptor for receiving said vessel, said adaptor having a fluid conduit member extending into the interior of said vessel when attached to said adaptor, and
      a flow control member selectively operable in a first flow control position enabling a flow path between a first pair of two ports and a second flow control position enabling a flow path between a second pair of two ports, said flow control member being coupled to one of said ports for manipulation between said flow control positions.

2. Applicator device according to claim 1, characterized in that said flow control member is rotatably mounted within the fluid control device.

3. Applicator device according to claim 1, characterized in that said adaptor is coupled to said flow control member for urging said flow control member from said first flow control position to said second flow control position upon rotation of said adaptor.

4. Applicator device according to claim 3, characterized in that said adaptor is integrally formed with said flow control member.

5. Applicator device according to claim 4, characterized in that said integrally formed adaptor cum flow control member includes a weakened portion enabling detachment of said adaptor from said flow control member after having urged said flow control member from said first flow control position to said second flow control position.

6. Applicator device according to claim 3, characterized in that said adaptor is coupled to said flow control member by interengaging means enabling detachment therebetween after having urged said flow control member from said first flow control position to said second flow control position.

7. Applicator device according to claim 1, characterized in that said at least one fluid control device further comprises a fourth port connectable to a medicinal vessel, said fourth port comprising an adaptor for receiving said vessel, said adaptor having a fluid conduit member extending into the interior of said vessel when attached to said adaptor.

8. Applicator device according to claim 1, characterized in that said adaptor or adaptors is/are provided for the attachment thereto of a vessel of the type of a vial, a glass bottle, an ampoule or an IV bag.

9. Applicator device according to claim 1, characterized in that said adaptor or adaptors is/are provided venting conduit for venting a medicinal vessel when attached thereto.

10. Applicator device according to claim 1, characterized in that a fluid control device is provided in each of the fluid connections between the front ends of the supply containers and the connectors of the connecting headpiece.

11. Applicator device according to claim 1, characterized in that the connecting headpiece is provided with a gas connector for supply of a medicinal gas, and with a channel extending from said gas connector to the outlet end.

12. Applicator device according to claim 1, characterized in that the outlet end of the connecting headpiece has a multi-lumen catheter connected thereto, the lumina of said multi-lumen catheter being flush with the channels ending on the outlet end of the connecting headpiece.

* * * * *